United States Patent
McNeil et al.

(10) Patent No.: US 11,322,234 B2
(45) Date of Patent: May 3, 2022

(54) AUTOMATED CONTENT AVOIDANCE BASED ON MEDICAL CONDITIONS

(71) Applicant: International Business Machines Corporation, Armonk, NY (US)

(72) Inventors: Kristin E. McNeil, Charlotte, NC (US); Robert C. Sizemore, Fuquay-Varina, NC (US); David B. Werts, Charlotte, NC (US); Sterling R. Smith, Apex, NC (US)

(73) Assignee: International Business Machines Corporation, Armonk, NY (US)

( * ) Notice: Subject to any disclaimer, the term of this patent is extended or adjusted under 35 U.S.C. 154(b) by 255 days.

(21) Appl. No.: 16/521,985

(22) Filed: Jul. 25, 2019

(65) Prior Publication Data

US 2021/0027868 A1    Jan. 28, 2021

(51) Int. Cl.
*G16H 10/60* (2018.01)
*G06N 20/00* (2019.01)
(Continued)

(52) U.S. Cl.
CPC ........... *G16H 10/60* (2018.01); *G06F 40/205* (2020.01); *G06F 40/242* (2020.01); *G06N 7/005* (2013.01); *G06N 20/00* (2019.01); *G16H 30/40* (2018.01)

(58) Field of Classification Search
CPC ...... G16H 10/60; G16H 30/40; G06F 40/205; G06F 40/242
(Continued)

(56) References Cited

U.S. PATENT DOCUMENTS 6,310,629 B1    10/2001  Muthusamy et al.
7,076,438 B1    7/2006   Tobelmann et al.
(Continued)

FOREIGN PATENT DOCUMENTS

CN    108647591 A    10/2018
CN    108765450 A    11/2018
(Continued)

OTHER PUBLICATIONS

List of IBM Patents or Patent Applications Treated as Related (Appendix P), Feb. 3, 2020, 2 pages.
(Continued)

*Primary Examiner* — Jason S Tiedeman
*Assistant Examiner* — Rachel F Durnin
(74) *Attorney, Agent, or Firm* — Stephen J. Walder, Jr.; Aaron Pontikos

(57) ABSTRACT

A medical condition based content filter mechanism is provided that analyzes patient information associated with a patient to identify medical condition(s) associated with the patient and correlating the medical condition(s) with one or more medical condition content indicator data structures specifying negative content indicators and/or positive content indicators. A user specific content indicator dictionary data structure (USCID) is generated based on the correlation and used to process received content to filter out portions of the content matching the negative content indicators or present portions of the content matching the positive content indicators, thereby generating modified content that is output to the patient via a content access application executing on a computing device associated with the patient.

20 Claims, 8 Drawing Sheets

(51) Int. Cl.
    *G16H 30/40*     (2018.01)
    *G06N 7/00*     (2006.01)
    *G06F 40/205*     (2020.01)
    *G06F 40/242*     (2020.01)

(58) Field of Classification Search
    USPC .......................................................... 705/2–3
    See application file for complete search history.

(56) References Cited

U.S. PATENT DOCUMENTS

| | | | |
|---|---|---|---|
| 9,495,957 | B2 | 11/2016 | Weider et al. |
| 9,616,568 | B1 | 4/2017 | Russell |
| 9,740,956 | B2 | 8/2017 | Chen et al. |
| 9,754,021 | B2 | 9/2017 | Byron et al. |
| 1,021,076 | A1 | 11/2018 | Chakraborty et al. |
| 10,121,256 | B2 | 11/2018 | Zhong et al. |
| 10,268,688 | B2 | 4/2019 | Dubbels et al. |
| 10,769,503 | B1 | 9/2020 | Buhler et al. |
| 2007/0050150 | A1* | 3/2007 | Levy ...................... G16H 20/70 702/19 |
| 2011/0125734 | A1 | 5/2011 | Duboue et al. |
| 2013/0226843 | A1 | 8/2013 | Syeda-Mahmood et al. |
| 2014/0058738 | A1 | 2/2014 | Yeskel |
| 2015/0100308 | A1 | 4/2015 | Bedrax-Weiss et al. |
| 2016/0203267 | A1* | 7/2016 | Mazonson ............. G16H 20/10 705/3 |
| 2016/0371587 | A1 | 12/2016 | Cao et al. |
| 2017/0124037 | A1 | 5/2017 | Hayashi et al. |
| 2017/0358256 | A1* | 12/2017 | Ross .................... G09G 3/3611 |
| 2018/0121618 | A1 | 5/2018 | Smith et al. |
| 2019/0022863 | A1 | 1/2019 | Kundu et al. |
| 2019/0080055 | A1 | 3/2019 | Bettencourt Da Silva et al. |
| 2019/0108912 | A1* | 4/2019 | Spurlock, III ......... G16B 40/20 |
| 2019/0141411 | A1* | 5/2019 | Byers ................ G06Q 30/0242 |
| 2019/0156821 | A1 | 5/2019 | Zamora Duran et al. |
| 2019/0156953 | A1* | 5/2019 | Chen ...................... G16H 50/30 |
| 2019/0342602 | A1* | 11/2019 | Aimone ............. H04N 21/4788 |

FOREIGN PATENT DOCUMENTS

| | | |
|---|---|---|
| CN | 109063723 A | 12/2018 |
| WO | WO2017201676 A1 | 3/2017 |

OTHER PUBLICATIONS

"Automatic Categorization of IT Infrastructure Service Management Data Using Natural Language Processing and Machine Learning", IPCOM000245200D, Disclosed Anonymously, Feb. 18, 2016, 7 Pages.

"Method and System for Dynamic Semantic Mapping With Machine Learning", IPCOM000252721D; Feb. 4, 2018, Disclosed Anonymously, 6 Pages.

"System and Method for Medical Cognitive Bias Analysis", IPCOM000254978D; Anonymously, Aug. 17, 2018, 4 Pages.

Ameur, Hanen et al., "Dynamic Construction of Dictionaries for Sentiment Classification", Dec. 2013, 9 Pages.

Khurana, Diksha et al., "Natural Language Processing: State of the Art, Current Trends and Challenges", 2017, 25 Pages.

Yao, Benspeng et al., "Recognizing Human-Object Interactions in Still Images by Modeling the Mutual Context of Objects and Human Poses", IEEE Transactions on Pattern Analysis and Machine Intelligence, vol. 34, No. 9, Sep. 2012, pp. 1691-1703.

High, Rob, "The Era of Cognitive Systems: An Inside Look at IBM Watson and How it Works", IBM Corporation, Redbooks, Dec. 12, 2012, 16 pages.

Yuan, Michael J., "Watson and healthcare, How natural language processing and semantic search could revolutionize clinical decision support", IBM Corporation, IBM developerWorks, http://www.ibm.com/developerworks/industry/library/ind-watson/, Apr. 12, 2011, 14 pages.

* cited by examiner

AUTOMATED CONTENT AVOIDANCE BASED ON MEDICAL CONDITIONS

BACKGROUND

The present application relates generally to an improved data processing apparatus and method and more specifically to mechanisms for automated content avoidance based on medical conditions.

In modern computing environments such as the Internet, computing tools are present to specifically track and analyze a user's interaction with content so that advertisers can target those individuals with advertisements designed to entice the individual to purchase a product or service, view specific content, or the like. For example, these tools may analyze various factors such as search histories, click-throughs, content viewing, electronic product purchases, electronic shopping cart contents, social networking posts, etc. to determine what types of items/services and/or content a user may be interested in and then present to them corresponding advertisements designed to entice them into performing an action to reward the advertiser, e.g., make a purchase, view content, etc.

In response, other computing tools have been developed to avoid such content, such as pop-up advertisement blockers, adult content blockers, and the like. These computing tools are keyed to broad categories of content, e.g., adult content, or to particular mechanisms for presenting the content, e.g., pop-ups, banner ads, etc. For example, through a user interface, a user may specify the types of content that they are interested in or the types of content that the user wishes to be filtered out, and these broad categories of content may be filtered or provided based on the user settings, e.g., a user setting to filter out "M" rated content will filter out all video game, movies, or other content that has an associated "M" rating attributed to it by an oversight authority.

SUMMARY

This Summary is provided to introduce a selection of concepts in a simplified form that are further described herein in the Detailed Description. This Summary is not intended to identify key factors or essential features of the claimed subject matter, nor is it intended to be used to limit the scope of the claimed subject matter.

In one illustrative embodiment, a method, in a data processing system comprising at least one processor and at least one memory, wherein the at least one memory comprises instructions that are executed by the at least one processor to configure the at least one processor to implement a medical condition based content filter engine. The method comprises analyzing, by the medical condition based content filter engine, patient information associated with a patient to identify one or more medical conditions associated with the patient. The method further comprises correlating, by the medical condition based content filter engine, the one or more medical conditions with one or more medical condition content indicator data structures. Each medical condition content indicator data structure comprises at least one of negative content indicators identifying content that negatively impacts a health of the patient, or positive content indicators identifying content that positively impacts the health of the patient. The method further comprises generating, by the medical condition based content filter engine, a user specific content indicator dictionary data structure based on results of the correlation by combining the one or more medical condition content indicator data structures correlated with the one or more medical conditions associated with the patient. In addition, the method comprises processing, by the medical condition based content filter engine, received content based on the user specific content indicator dictionary data structure, to at least one of filter out portions of the content matching the at least one negative content indicator or present portions of the content matching the at least one positive content indicator, thereby generating modified content. Moreover, the method comprises outputting, by the medical condition based filter content filter engine, the modified content to the patient via a content access application executing on a computing device associated with the patient.

In other illustrative embodiments, a computer program product comprising a computer useable or readable medium having a computer readable program is provided. The computer readable program, when executed on a computing device, causes the computing device to perform various ones of, and combinations of, the operations outlined above with regard to the method illustrative embodiment.

In yet another illustrative embodiment, a system/apparatus is provided. The system/apparatus may comprise one or more processors and a memory coupled to the one or more processors. The memory may comprise instructions which, when executed by the one or more processors, cause the one or more processors to perform various ones of, and combinations of, the operations outlined above with regard to the method illustrative embodiment.

These and other features and advantages of the present invention will be described in, or will become apparent to those of ordinary skill in the art in view of, the following detailed description of the example embodiments of the present invention.

BRIEF DESCRIPTION OF THE SEVERAL VIEWS OF THE DRAWINGS

The invention, as well as a preferred mode of use and further objectives and advantages thereof, will best be understood by reference to the following detailed description of illustrative embodiments when read in conjunction with the accompanying drawings, wherein.

DETAILED DESCRIPTION

Figure 1A:
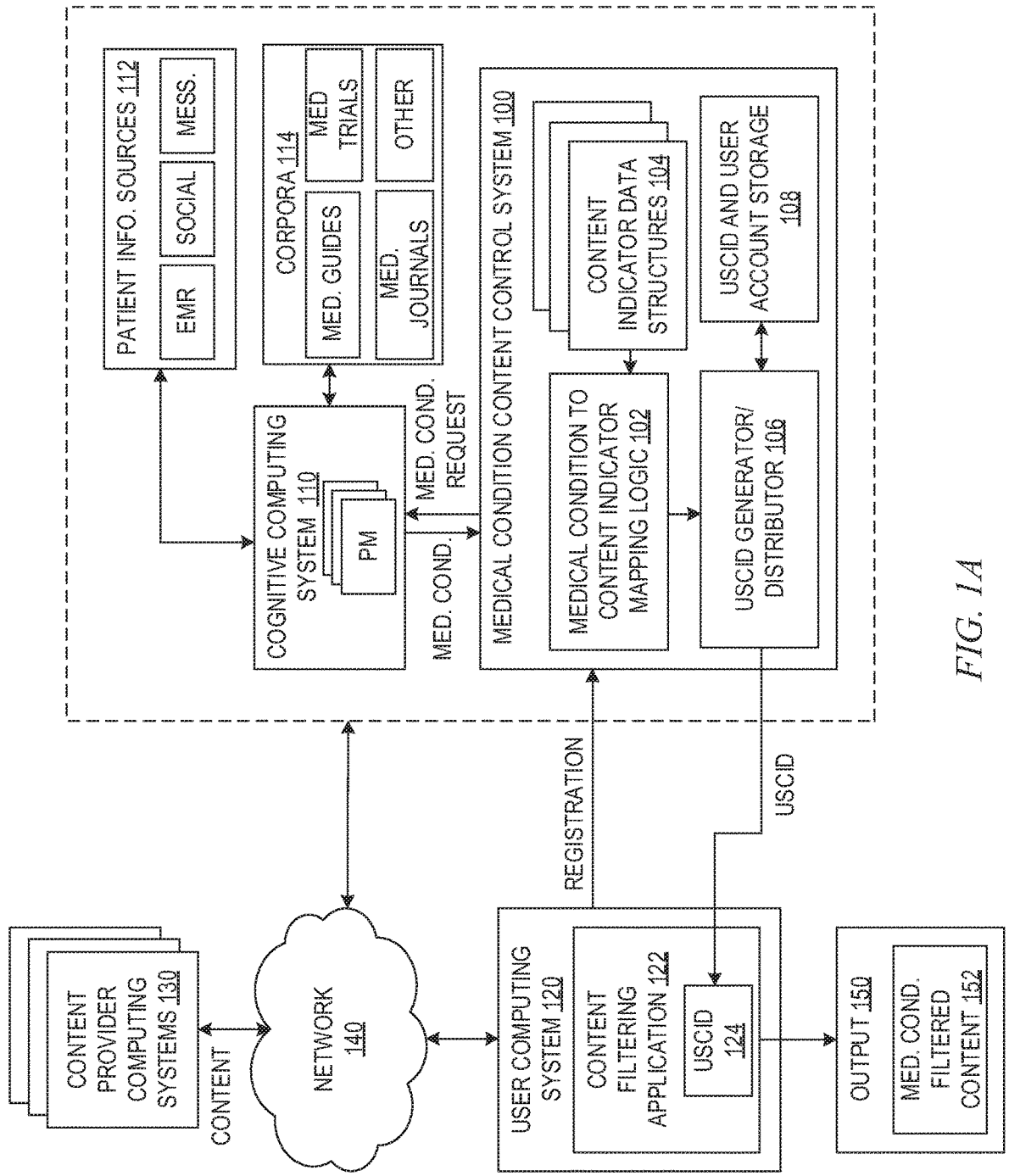
FIG. 1A is an example diagram illustrating an interaction of primary operational elements of a medical condition content control system in accordance with one illustrative embodiment in which a filtering application is deployed in an end user computing system.

The illustrative embodiments provide mechanisms for automatic content avoidance based on automatically determined medical conditions of a user. The mechanisms of the illustrative embodiments integrate cognitive computing evaluations of the electronic medical records of a user to determine medical conditions afflicting the user, with content filtering or avoidance so as to assist the user in avoiding content that may exacerbate or perpetuate the user's medical condition(s). That is, content that may affect a user's behavior so as to promote behaviors that negatively affect the user's health with regard to the user's personal medical condition(s) are filtered/blocked/replaced, while content that may affect a user's behavior so as to promote behaviors that are positive and promote improved health of the user with regard to their personal medical condition(s) are permitted to be accessed by the user. Thus, the mechanisms of the illustrative embodiments provide an automated computing tool for tailoring content filtering automatically to the medical conditions of the user.

As noted above, there are computing tools that allow a user to specify what content to filter and/or provide to the user through the user's setting of preferences, with the settings being based on broad categories of content. While the user may specify broad types of content that they desire to view and/or block, such content filtering is directed by the user themselves and subject to the user's own behavioral self-control. As a result, these mechanisms are easily circumvented and subject to the user's own honesty/dishonesty with themselves and with the content filtering providers, which can be problematic for users suffering from medical conditions that are tied to their behaviors, e.g., alcoholism, smoking, diabetes, obesity, etc. Unfortunately, users are inundated with content on a daily basis and users may not be able to determine a priori which content items have elements that will trigger negative behaviors that will exacerbate or perpetuate their own medical conditions. Placing the burden on the end user to determine each and every type of content that may be detrimental to their health is a faulty solution due to human limitations in both knowledge and self-control.

Known content filtering mechanisms do not provide any mechanism for automatically tailoring the mechanisms to particular individual's medical condition(s) based on an evaluation of medical information about that individual. That is, individuals may have medical conditions that may be exacerbated or perpetuated by the presentation of particular content via their computing and/or communication devices which seek to trigger behaviors that, for that particular user, are negative given the user's personal medical condition(s), but may not be negative for other users that are not suffering from the same medical condition(s). For example, persons that have alcoholism should avoid content that references alcohol, obese individuals should avoid content referencing high caloric or unhealthy food choices, a smoker should avoid content containing references to tobacco products, etc. These types of content may exacerbate or perpetuate the medical condition(s) of the user as they expose the user to products/services that play to the negative behavioral aspects associated with the medical condition of the user. While the content provider may be purposefully attempting to target individuals with such medical condition(s), and other users may not be triggered by such content, such content may be a trigger for particular users whose medical condition(s) make them susceptible. That is, such considerations of content that are triggers for behaviors that negatively affect a user's medical condition(s) are personal to each user based on their own specific medical condition(s).

The present invention provides a mechanism for automatically learning, through a cognitive computing evaluation of a user's electronic medical records, social networking posts or communications, electronic messages, etc., a user's medical condition(s), correlating that information with indicators of content to avoid based on user behavioral aspects of the user's medical condition(s), and content control applications for accessing content so as to avoid or replace the negative influence content with positive influence content that will not tend to cause user behavior that exacerbates or perpetuates the user's medical condition(s). The illustrative embodiments of the present invention use a cognitive computing system to evaluate a user's medical condition based on a cognitive evaluation of the user's electronic medical records, social networking interactions, electronic mail communications, instant messaging communications, and the like, which are collectively referred to herein as "patient information." That is, "patient information" comprises data from any source computing system that provides structured or unstructured content about, or generated by, a user of interest and may contain information that, through a cognitive computing operation of a cognitive computing system, indicates a medical condition of the user of interest.

For example, electronic medical records (EMRs) associated with the user, and which may come from a variety of sources including doctor office computing systems, hospital computing systems, pharmacy computing systems, medical insurance provider computing systems, etc., provide medical information about the user which can be processed by the cognitive computing system, such as via natural language processing mechanisms, to extract features indicative of medical conditions, e.g., medical codes, medical terms/phrases in notes entered by medical personnel, vital sign values, medical lab results (both numeric values and/or textual descriptions), features of medical images obtained through image analysis, etc. Similarly, social networking posts to social networking websites may be processed via natural language processing and the like to extract features that are indicators of medical conditions, e.g., a user may complain of insomnia on a social networking website even though their EMR may not have yet documented insomnia as a medical condition for the user. The features extracted from the patient information from these various sources may be evaluated by the cognitive computing system to draw inferences from these features as to the probability that particular medical conditions apply to the user and thereby correlates combinations of extracted features with particular medical conditions. If the probability value is greater than a predetermined threshold probability, it may be determined that the medical condition(s) apply to the user.

It should be appreciated that temporal considerations may also be included in the determination of medical condition(s) associated with the user since a number of medical conditions may be long term medical conditions while other medical conditions may be more fleeting, e.g., insomnia may be a temporary condition while diabetes is a more long term condition. Thus, a cognitive evaluation of patient information may taken into consideration the timestamps and/or temporal indicators associated with patient information when determining what medical condition(s) apply to the patient currently. Hence, the evaluation of what medical condition(s) apply to the patient is performed with regard to the current time and such evaluations may be performed periodically over time so as to dynamically adjust the understanding of what medical condition(s) are associated with the user as the user's health improves/declines over time.

The medical condition(s) identified through the cognitive computing system's evaluation of the patient information may be any condition that affects the physical and/or mental health of the user, including medical problems (e.g., obesity, diabetes, heart conditions, high blood pressure, etc.), behavior conditions (e.g., negative habits, overeating, alcoholism, drug addiction, etc.) and psychological conditions (e.g., phobias, compulsions, etc.). These medical condition(s) may have human behaviors associated with them that may exacerbate or perpetuate the medical condition. For example, obesity may have human behaviors such as eating unhealthy foods, a sedentary lifestyle, and the like, that are associated with the medical condition. It is these human behaviors that the content filtering/blocking/replacing of the illustrative embodiments seeks to influence by exposing the user to content that promotes products, services, information, entertainment, etc. that results in user behaviors that tend to improve the user's health while demoting or avoiding content that results in user behaviors that tend to perpetuate or worsen a medical condition.

The medical conditions associated with the user are correlated with medical conditions for which data structures have been defined that specify the particular terms/phrases, metadata, data annotations, or other indicators of content which are indicative of negative/positive content for the user. Negative content is content that has been determined to be likely to promote behaviors, purchases, activities, or other actions by the user that will negatively impact the user's physical or mental health, e.g., temptations, or otherwise perpetuate the user's medical condition. Positive content is content that is determined to be likely to promote behaviors, purchases, activities, or other actions by the user that will positively impact the user's physical or mental health. These term/phrases, metadata, data annotations, etc. are referred to herein as content indicators and may include both positive content indicators and negative content indicators. Thus, by correlating the medical conditions with content indicator data structures specifying the positive and/or negative content indicators, the mechanisms of the illustrative embodiments determine what to look for when identifying positive/negative content that is attempting to be presented to a user having the corresponding medical conditions.

A user specific content indicator dictionary (USCID) data structure specifying the particular negative/positive content indicators for the user's medical condition(s) is generated for the specific user based on the correlation of the medical conditions of the user with the predefined content indicator data structures. The USCID data structure may differ from the content indicator data structures in that it may be a combination of multiple content indicator data structures depending on how many medical conditions the user is identified as having. In some cases, the USCID data structure may be the same as a single content indicator data structure, e.g., the only medical condition determined for the user is "smoker" based on an analysis of the user's patient information, e.g., results of an online medical questionnaire may include an answer from the user indicating the user has smoked within the last 2 months. In other cases, the user may be determined to have multiple medical conditions, e.g., diabetes, smoker, and obesity, in which case the USCID data structure may comprise content indicators from multiple content indicator data structures, each associated with a different medical condition determined to be afflicting the user.

The USCID data structure may be installed in specific applications executing on the user's client computing device, associated with the user's account at a server computing device, provided in an agent application on the client computing device, or otherwise associated with applications used to access content. These applications may comprise various mechanisms for accessing content, such as Internet browser applications, video playback applications, electronic mail applications, instant messaging applications, social networking website application, and the like. These various applications may be provided with interfaces through which they are able to access the USCID data structure for the user and control presentation of content to the user by filtering/replacing content matching negative content indicators and including content matching positive content indicators in the content that is accessed by the user via the corresponding application.

In some embodiments, the USCID data structure is used by a dedicated filtering application executing on the corresponding computing device, e.g., client computing device or server computing device, and content traffic flowing to/from the computing device is examined and filtered, and optionally replaced, based on the USCID data structure for the user to whom the content is directed. That is, a user may log onto or otherwise identify themselves as utilizing a computing device with which the content filtering application is operating. In response, the content filtering application may retrieve USCID data structures associated with the user, e.g., from a user account associated with the content filtering application. If the USCID data structure has not been updated within a predetermined period of time, then an update of the USCID data structure may be initiated by performing again a cognitive computing system analysis of the patient information for the user to determine the user's current medical condition(s) and correlating those with content indicator data structures, e.g., the user's medical conditions may have changed since a last update of the USCID data structure. The USCID data structure for the user is then installed in the content filtering application for use during a current communication session so as to filter content flowing to the user via the computing device.

With regard to the filtering, the content indicators in the USCID data structure are used to compare with content indicators identified in content through a processing of the content prior to it being output to the user. For example, the metadata for the content may be analyzed to extract any terms/phrases or other content indicators, if the content comprises text, the text may be analyzed using natural language processing to extract terms/phrases indicative of content, if the content comprises an image, image analysis may be applied to determine what objects are present in the image and categorize them with regard to content indicators, etc. Thus, content indicators extracted from the content may be compared to the content indicators present in the USCID data structure to determine if there are any matches. Based on whether or not the match is a negative content indicator or positive content indicator match, different filtering/replacement operations may be performed. For example, if the match is a negative content indicator match, then the content may be blocked or filtered out such that it is not output to the user. Portions of the content that are not associated with the negative content indicator may still be provided to the user. If the match is a positive content indicator match, then the content may be permitted to be output to the user.

In some cases, content matching negative content indicators may be replaced with content matching positive content indicators. That is, content providers may register their content with the filter application provider or content filter service provider as alternatives to negative content and may specify the positive content indicators with which their content corresponds. A mapping of negative content indicators and corresponding positive content indicators may be provided that indicates for particular negative content indicator a positive content indicator that can be used to replace the content associated with the negative content indicator. Thus, if a negative content indicator is matched by content that is to be provided to the user, the negative content indicator may be mapped to a positive content indicator, which may then be used to search for alternative content to be output to the user. The alternative content may then be swapped in as a replacement for the content corresponding to the negative content indicator, e.g., for a user having diabetes, an advertisement for a sugary product, e.g., a candy bar, may be replaced with an advertisement for a healthier and non-sugary snack, such as nuts.

Thus, for example, in an Internet Browser, advertisements appearing on web pages may be processed with the mechanisms of the illustrative embodiments to determine whether the advertisements have negative content or positive content for the particular user based on the user's medical conditions. For example, a user that suffers from alcoholism should not be exposed to advertisements about vodka, beer, or other alcoholic beverages, places whose primary business is the sale of such beverages, or the like. Similarly, users having diabetes should not be presented with advertisements specifying sugary foods, users suffering from obesity should not be presented with advertisements for fast food, unhealth snacks, and the like, users that are smokers should have advertisements for cigarettes and smoking products filtered out or replaced, etc. Similar identifying of advertisements that are positive for the user may be identified and permitted to be accessed by the user, e.g., vegetarian users may be presented with content advertising vegetarian products, e.g., cookbooks, meat substitutes, etc., diabetes users may be presented with advertisements directed to controlling blood sugar levels, etc.

With the mechanisms of the illustrative embodiments, the existence of such medical conditions is automatically determined through the cognitive computing system's evaluation of user information, e.g., user electronic medical records, social networking interactions, electronic mail communications, instant messaging communications, etc. The user may voluntarily enroll in automated content filtering based on their medical conditions so as to allow the mechanisms of the illustrative embodiments to automatically determine the user's medical conditions and perform automated content filtering and/or replacement based on the automatically determined user medical conditions. Thus, when the cognitive computing system determines that the user has a particular medical condition, the corresponding user specific dictionary is generated based on the correlation of the medical condition with negative/positive content indicators, and then the user's specific dictionary is deployed to appropriate content presentation applications for use in filtering/replacing content. In this way, the mechanisms of the illustrative embodiments protect the user from content that may negatively affect the user's physical/mental health and may replace such content with content that positively affects the user's physical/mental health.

In some illustrative embodiments, the filtering of content may be performed within multi-media content so as to filter out individual portions of the multi-media content from the remainder of the content. For example, within a movie, scenes may be associated with corresponding metadata that indicates the content of those scenes. Based on the correlation of the metadata for the scenes with the user's dictionary, some scenes in the movie may be filtered out, e.g., skipped during playback, and the like. For example, scenes depicting drug use, scenes depicting smoking, or the like, may be automatically filtered out or skipped during playback for users having corresponding medical conditions. Thus, the mechanisms of the illustrative embodiments may be integrated with other currently existing or later developed computer tools for such media content filtering including, for example, Clearplay®, Vidangel®, or the like. For example, the USCID data structures may be used to configure such media content filtering tool settings so as to inform the tool what content to filter out or block from viewing by the particular user. In this way, the media content filtering is automatically configured according to the sensitivities of the particular medical conditions associated with the user. As noted above, this determination may be dynamically updated such that the media content filtering tool is dynamically reconfigured as the medical conditions currently afflicting the user change over time.

Thus, with the mechanisms of the illustrative embodiments, automated computing tools are provided for determining a user's medical conditions, what content indicators correspond to negative/positive influences on the user's determined medical conditions, and then using these indicators to automatically filter and/or replace portions of content presented to a user so as to minimize negative influences on the user's physical/mental health while promoting positive influences on the user's physical/mental health. With the mechanisms of the illustrative embodiments, the user need only assent to the general use of computing tools to assist them in improving or maintaining the user's physical/mental health and the automated computing tools may then make the determinations as to what content negatively/positively influences the particular medical conditions of the user as determined through automated cognitive analysis of the user's information. In some illustrative embodiments, greater controls may be presented to the user so that they can more specifically identify what control they are willing to hand over to the automated computing tools, such as via a user interface or the like that provides user selectable options for providing permissions both with regard to the filtering/replacement of content and with regard to accessing particular types and/or sources of user information in order to determine medical conditions affecting the user.

Before beginning the discussion of the various aspects of the illustrative embodiments in more detail, it should first be appreciated that throughout this description the term "mechanism" will be used to refer to elements of the present invention that perform various operations, functions, and the like. A "mechanism," as the term is used herein, may be an implementation of the functions or aspects of the illustrative embodiments in the form of an apparatus, a procedure, or a computer program product. In the case of a procedure, the procedure is implemented by one or more devices, apparatus, computers, data processing systems, or the like. In the case of a computer program product, the logic represented by computer code or instructions embodied in or on the computer program product is executed by one or more hardware devices in order to implement the functionality or perform the operations associated with the specific "mechanism." Thus, the mechanisms described herein may be implemented as specialized hardware, software executing on general purpose hardware, software instructions stored on a medium such that the instructions are readily executable by specialized or general purpose hardware, a procedure or method for executing the functions, or a combination of any of the above.

The present description and claims may make use of the terms "a", "at least one of", and "one or more of" with regard to particular features and elements of the illustrative embodiments. It should be appreciated that these terms and phrases are intended to state that there is at least one of the particular feature or element present in the particular illustrative embodiment, but that more than one can also be present. That is, these terms/phrases are not intended to limit the description or claims to a single feature/element being present or require that a plurality of such features/elements be present. To the contrary, these terms/phrases only require at least a single feature/element with the possibility of a plurality of such features/elements being within the scope of the description and claims.

Moreover, it should be appreciated that the use of the term "engine," if used herein with regard to describing embodiments and features of the invention, is not intended to be limiting of any particular implementation for accomplishing and/or performing the actions, steps, processes, etc., attributable to and/or performed by the engine. An engine may be, but is not limited to, software, hardware and/or firmware or any combination thereof that performs the specified functions including, but not limited to, any use of a general and/or specialized processor in combination with appropriate software loaded or stored in a machine readable memory and executed by the processor. Further, any name associated with a particular engine is, unless otherwise specified, for purposes of convenience of reference and not intended to be limiting to a specific implementation. Additionally, any functionality attributed to an engine may be equally performed by multiple engines, incorporated into and/or combined with the functionality of another engine of the same or different type, or distributed across one or more engines of various configurations.

In addition, it should be appreciated that the following description uses a plurality of various examples for various elements of the illustrative embodiments to further illustrate example implementations of the illustrative embodiments and to aid in the understanding of the mechanisms of the illustrative embodiments. These examples intended to be non-limiting and are not exhaustive of the various possibilities for implementing the mechanisms of the illustrative embodiments. It will be apparent to those of ordinary skill in the art in view of the present description that there are many other alternative implementations for these various elements that may be utilized in addition to, or in replacement of, the examples provided herein without departing from the spirit and scope of the present invention.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Java, Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As noted above, the present invention provides a mechanism for automatically determining the medical conditions associated with a user and associating those medical conditions with content indicators that indicate which types of content have positive/negative influences on those medical conditions. These content indicators are then used to filter/block/replace content that is attempting to be output to the user so as to promote positive influence content while minimizing negative influence content.

FIG. 1A is an example diagram illustrating an interaction of primary operational elements of a medical condition content control system in accordance with one illustrative embodiment in which a filtering application is deployed in an end user computing system. As shown in FIG. 1A, the primary operational elements comprise the medical condition content control system 100, a cognitive computing system 110, and a deployed content filtering application 122. These elements are shown as separate elements in FIG. 1A which may be implemented on the same or different computing devices. For example, the cognitive computing system 110 may be implemented in a first server computing system which operates to evaluate patient information 112 based on knowledge resources present in the corpora 114 using trained predictive models (PMs), as described in greater detail hereafter. The medical condition content control system 100 may be implemented on a second server computing system, potentially remotely located from the first server computing system, and operates to take the medical conditions identified by the cognitive computing system 110 and determining which content indicators apply to the medical conditions of the user so as to generate and distribute a user specific content indicator dictionary (US-CID) data structure 124 for a user to appropriate computing devices in which content filtering applications 122 are deployed. In some illustrative embodiments, the first and second server computing devices may be the same server computing device implementing both the cognitive computing system 110 and the medical condition content control system 100. In still other illustrative embodiments, the cognitive computing system 110, medical condition content control system 100, and content filtering application 122 may be implemented in the same computing device or computing system which may be a server computing system or an end user computing system, such as user computing system 120.

The various computing systems/devices, e.g., cognitive computing system 110, medical condition content control system 100, and user computing system 120, as well as other computing systems/devices such as content provider computing systems 130, patient information sources 112, and corpora 114 providing computing systems, may be in data communication with one another via one or more computing networks 140. Thus, the communication pathways represented by arrows in FIG. 1A may in fact be data communication pathways that flow through the one or more networks 140. These communication pathways may implement communication interfaces, data security mechanisms, e.g., encryption/decryption, and the like, to facilitate secure communications where necessary so as to ensure the privacy of data associated with a user.

As shown in FIG. 1A, a user of a user computing system 120 may log onto or otherwise access the medical condition content control system 100 so as to register with the medical condition content control system 100 for automated medical condition content filtering/blocking/replacement. As part of the registration process, the user may enter information about themselves, including identifiers which may be used to access patient information for the user from various patient information sources 112. The registration process may further include the user assenting to legal requirements to allow access to the user's patient information and its use in performing the medical condition content filtering/blocking/replacement. The registration process may also include answering questions in one or more medical condition questionnaires or the like, so as to establish a baseline understanding of the user's medical condition at the time of registration, which may then be modified or augmented by the results of the cognitive computing operations performed by the cognitive computing system 110 on the patient information for the user from the patient information sources 112 using the knowledge resources from the corpora 114.

Responsive to the registration operation being complete, or at various times when dynamic updating of medical conditions associated with a user is appropriate, e.g., after a predetermined period of time since a last update of the user's medical conditions, the cognitive computing system 110 is employed to determine what medical conditions are associated with a registered user. The cognitive computing system 110 comprises one or more predictive computer models (PMs) that have been trained through a machine learning training operation based on the corpora 114 which includes electronic documents that may comprise content of medical guidelines, medical trials reports, medical journals and other sources of medical knowledge.

The cognitive computing system 110 obtains patient information from the various patient information sources 112, extracts features from this patient information, and applies the knowledge learned through training of the PMs from the corpora 114 to thereby learn a health state of a user, e.g., the medical condition(s) associated with the user. The cognitive computing system 110 is a computing system that implements a technology platform that is based on scientific principles of artificial intelligence and signal processing. Examples of such technology platforms encompass machine learning, machine reasoning, natural language processing, speech recognition, computer vision (object recognition), human-computer interaction, dialog and narrative generation, and the like. Thus, the cognitive computing system may comprise a machine learning mechanism, employing one or more predictive models (PMs), which may be used to learn associations of features extracted from patient information that are indicative of particular medical conditions. These predictive models may comprise any of a variety of different machine learning or deep learning mechanisms which may be trained through a variety of machine learning techniques.

As an overview, a cognitive system is a specialized computer system, or set of computer systems, configured with hardware and/or software logic (in combination with hardware logic upon which the software executes) to emulate human cognitive functions. These cognitive systems apply human-like characteristics to conveying and manipulating ideas which, when combined with the inherent strengths of digital computing, can solve problems with high accuracy and resilience on a large scale. A cognitive system performs one or more computer-implemented cognitive operations that approximate a human thought process as well as enable people and machines to interact in a more natural manner so as to extend and magnify human expertise and cognition. A cognitive system comprises artificial intelligence logic, such as natural language processing (NLP) based logic, for example, and machine learning logic, which may be provided as specialized hardware, software executed on hardware, or any combination of specialized hardware and software executed on hardware. The logic of the cognitive system implements the cognitive operation(s), examples of which include, but are not limited to, question answering, identification of related concepts within different portions of content in a corpus, intelligent search algorithms, such as Internet web page searches, for example, medical diagnostic and treatment recommendations, and other types of recommendation generation, e.g., items of interest to a particular user, potential new contact recommendations, or the like.

It should be appreciated that even though the cognitive computing system attempts to approximate or emulate the human thought processes, the way that computers operate is significantly different than the human mind due to the nature of computers requiring explicit instructions in order to perform operations. For example, while a human mind may see a picture of a cat and be able to intuitively know that the picture is one of a cat, a cognitive computing system performing image recognition operations must have logic and be trained to recognize certain combinations of characteristics of the image data as representative of a cat and properly classify it as such. Thus, while human thought processes may be emulated, the computer operation is a completely different operation from that of a human mind, even though the result may appear to be similar. Ingenuity is required to make a cognitive computing system emulate human thought processes due to this fundamental difference in the way a human mind and a computer operate.

IBM Watson™ is an example of one such cognitive computing system which can process human readable language, digital images in some implementations, audible inputs in some implementations, and the like, and generate cognitive operation results, e.g., classifications of input data, recognition of objects in digital images, determinations of operations to be performed based on input data, recommendations for subsequent action, etc. based on inferences that the cognitive computing system generates from the features extracted from the various inputs and reference data processed by the cognitive computing system based on its machine learning training. In the realm of processing human readable language, in some implementations IBM Watson™ may evaluate unstructured natural language content in text passages and identify inferences between text passages with human-like high accuracy at speeds far faster than human beings and on a larger scale. In general, cognitive computing systems, depending on the specific implementation, are able to perform the following functions: navigate the complexities of human language and understanding; ingest and process vast amounts of structured and unstructured data; generate and evaluate hypotheses; weigh and evaluate responses that are based only on relevant evidence; provide situation-specific advice, insights, and guidance; improve knowledge and learn with each iteration and interaction through machine learning processes; enable decision making at the point of impact (contextual guidance); scale in proportion to the task; extend and magnify human expertise and cognition; identify resonating, human-like attributes and traits from natural language; deduce various language specific or agnostic attributes from natural language; high degree of relevant recollection from data points (images, text, voice) (memorization and recall); predict and sense with situational awareness that mimic human cognition based on experiences; answer questions based on natural language and specific evidence.

Examples of cognitive computing systems employing predictive models which may be used to determine the health state of a user, e.g., the medical conditions associated with a user, are described in commonly owned U.S. Patent Application Publications 2019/0080055 and 2014/0058738. Other types of cognitive computing systems, currently known or later developed, that employ predictive models for determining predictions of medical conditions affecting a user may be used without departing from the spirit and scope of the present invention. These predictive models may take many different forms including neural networks, decision trees structures, deep learning computing systems, and the like.

As shown in FIG. 1A, in response to the user's registration with the medical condition content control system 100, at periodic times when medical condition information may be determined to be "stale", e.g., after a predetermined amount of time since a last update of the user's medical conditions, or in response to a trigger event, such as an update to the user's electronic medical records, the medical condition content control system 100 sends a medical condition request to the cognitive computing system 110 that specifies the identity of the user and sets forth a request for updated medical condition information for that user. The cognitive computing system 110 retrieves the patient information for the user from the patient information sources 112 and processes the patient information via the predictive models to determine which medical conditions apply to the user based on the current state of the patient information. The predictive models of the cognitive computing system 110 may be specifically trained to identify particular medical conditions such that multiple predictive models may be implemented by the cognitive computing system 110 and applied to the patient information.

The cognitive computing system 110 compiles the results of the processing from the various PMs to generate a listing of medical conditions that are determined to be associated with the user. The listing of medical conditions, which may comprise zero or more medical conditions, is returned to the medical condition content control system 100. The medical condition to content indicator mapping logic 102 of the medical condition content control system 100 maps the medical conditions identified by the cognitive computing system 110 as being associated with the user are mapped to content indicators by retrieving content indicator data structures 104 associated with the medical conditions. That is, for each potential medical condition handled by the medical condition content control system 100, a predetermined content indicator data structure 104 is generated and stored for use in mapping content indicators to medical conditions associated with users. Thus, for example, a first content indicator data structure 104 may be provided for type 2 diabetes, a second content indicator data structure 104 may be provided for obesity, a third content indicator data structure 104 may be provided for smoking, etc. The medical conditions in the listing of medical conditions provided by the cognitive computing system 110 are matched or mapped to the corresponding content indicator data structures 104 which are then provided to the user specific content indicator dictionary (USCID) generator/distributor 106.

The USCID generator/distributor 106 generates a USCID by combining the content indicator data structures 104 that correspond to the medical conditions associated with the user. The content indicator data structures 104 comprise content indicators for negative content, positive content, or a combination of negative and positive content. The content indicators may comprise various types of indicators such as specific text/phrases, medical codes, metadata, or any other indicator that specifies a type of content and specifically a type of content corresponding to medical conditions. The resulting USCID may be stored in association with the user's account, established during registration, in the USCID and user account storage 108 for later retrieval, update, and providing to content filtering applications.

The USCID generator/distributor 106 may also operate to distribute the generated USCID to one or more content filtering applications 122 on one or more computing systems responsible for providing and/or outputting content. In the depicted example of FIG. 1A, the content filtering application 122 is deployed to the user computing system 120 that is the computing system operated by the user when accessing content from one or more content provider computing systems 130 via the network 140. The USCID 124 distributed by the USCID generator/distributor 106 is installed in the content filtering application 122 which configures that content filtering application 122 to use the content indicators to control the output of content to the user in recognition of the medical conditions associated with that user. Thus, for example content received from the content provider computing system 130 may be processed by the content filtering application 122 to determine if there are any portions of content associated with content indicators matching negative influence content indicators in the USCID 124. In such a case, the content filtering application 122 may remove, block, or replace such portions of content prior to outputting the content to the user as output 150 with the medical condition filtered content 152.

Thus, with these mechanisms, the output 150 to the user comprises medical condition filtered content 152 where content that is automatically determined to be likely to influence negative behaviors, relative to the medical conditions of the user, are automatically removed, blocked, or replaced with content that is determined to be more likely to influence positive behaviors. In some cases, the content that is filtered/blocked may be replaced with placeholder content indicating the fact that the original content has been removed and the reasoning why the content was removed, e.g., "this content has been removed because it may negatively impact your medical condition." In some cases, the user may be presented with user interface controls whereby the user may override the content filtering/blocking with regard to the particular filtered/blocked content, e.g., a user interface element that is selectable by the user, possibly with the entry of a password, personal identification number, or the like, such that the user may override the content filtering/blocking and the original content may then be rendered and provided as part of an updated output 150. While this provides a mechanism for avoiding the content filtering/blocking, it requires that the user take active steps to override making the user think about what they are doing and whether they really want to expose themselves to something that may be detrimental to their medical conditions.

In order to obtain such benefits, the user need only register and assent to automated medical condition content controls and allow the automated systems to determine which content falls within the categories of negative/positive influences for the user's medical conditions. This alleviates the burden on users to police the content being provided to them, which is especially cumbersome in modern computing environments where content is constantly being pushed to end users sometimes without their prior knowledge or consent. While some amount of control is given up to the automated mechanisms, the automated mechanisms provide protections that the user may not otherwise be able to enjoy without significant personal efforts.

Figure 1B:
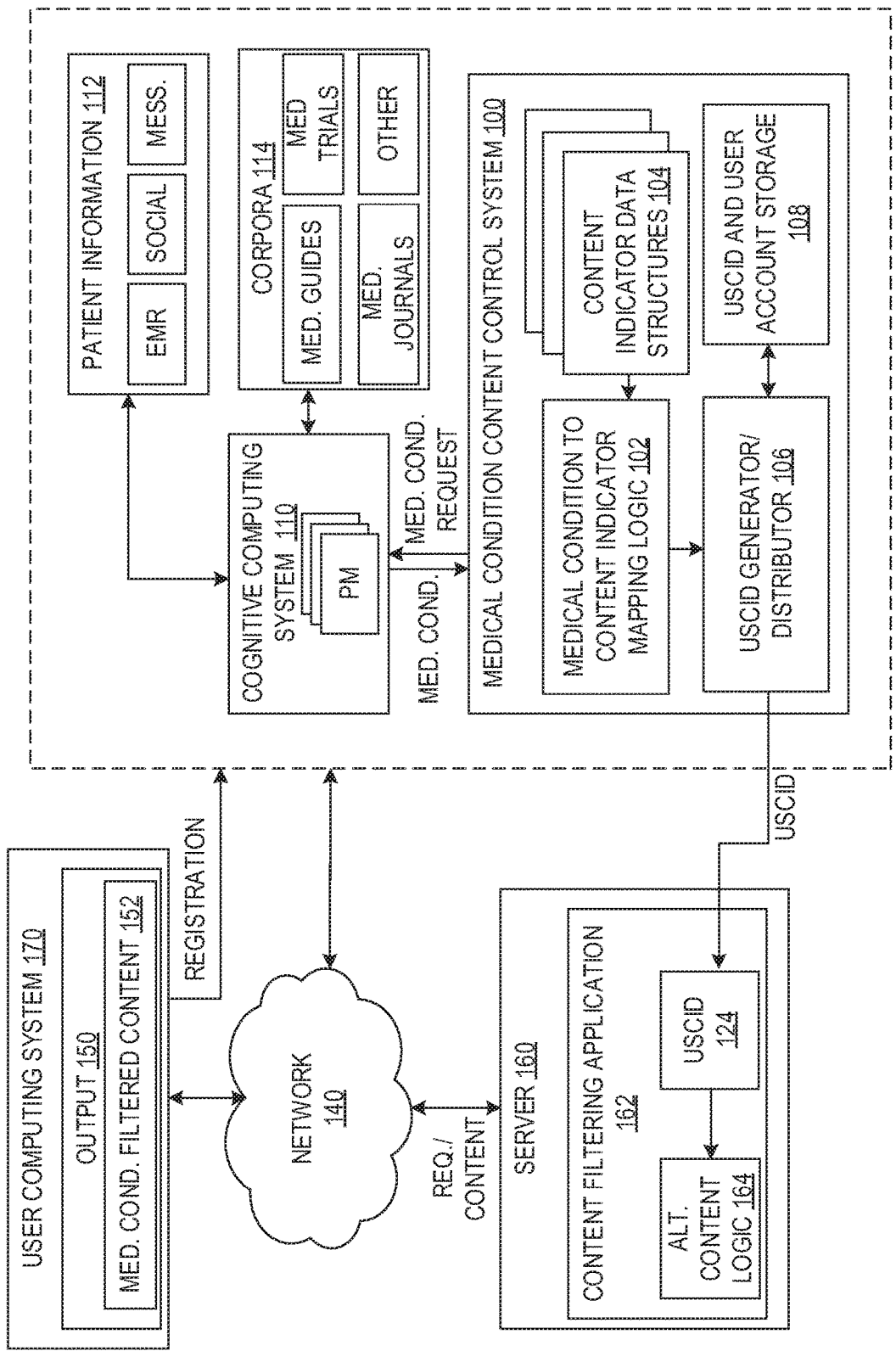
FIG. 1B is an example diagram illustrating an interaction of primary operational elements of a medical condition content control system in accordance with one illustrative embodiment in which a filtering application is deployed in a content server computing system.

As noted above, FIG. 1A depicts one example embodiment in which the content filtering application is deployed in the end user computing system such that the content filtering/blocking/replacement is performed at the point where the content is being output. FIG. 1B is an example diagram illustrating an interaction of primary operational elements of a medical condition content control system in accordance with one illustrative embodiment in which a filtering application is deployed in a content server computing system. By deploying the content filtering application in the server computing system, the content filtering/blocking/replacement may be performed closer to the sources of content and facilitates the ability to identify replacement content that is associated with positive content indicators associated with the medical conditions of the user.

The configuration shown in FIG. 1B differs from that of FIG. 1A in that the content filtering application 162 is implemented in server 160 and further comprises an alternative content logic 164 for selecting alternative content for content having content indicators that match negative influence content indicators specified in the USCID 124 for a user. The server 160 may be a content provider server which operates to provide content to end users via their user computing systems 170 and one or more data networks 140. The server 160, in some embodiments, may be a gateway server that serves as an intermediary between the user computing systems 170 and content provider servers. The server 160, in some embodiments, may be an Internet service provider computing system that provides a pathway by which user computing systems 170 are able to access content on the Internet.

In the depicted embodiment in FIG. 1B, similar to the description of FIG. 1A above, the USCID 124 is generated by the medical condition content control system 100 and distributed to the content filtering application 162. When content is flowing to the user computing system 170 through the server 160, the content filtering application 162 compares content indicators associated with the content to content indicators specified in the USCID 124. The USCID 124 may comprise both negative content indicators and positive content indicators. In response to content having content indicators matching a negative content indicator, the positive content indicators may then be used by the alternative content logic 164 to select alternative content, having content indicators matching positive content indicators in the USCID 124, to replace the content associated with the negative content indicator. The alternative content may be pre-registered with the server 160 and its corresponding content indicators registered with the alternative content logic 164 of the content filtering application 162. As a result, the matching of positive content indicators in the USCID 124 with content indicators of the pre-registered content may be performed and the corresponding content retrieved and used to replace the negative influence content. In some illustrative embodiments, the particular positive content indicators used may be those that correspond to the same medical condition as the negative content indicator matched by the content that is filtered out/blocked.

Thus, with the mechanisms of this illustrative embodiment, not only is negative influence content filtered/blocked based on the medical conditions associated with the user, but this negative influence content may be replaced with positive influence content that is determined to have a positive influence on user behaviors associated with the user's medical conditions. Hence, not only does the system help avoid negative influences, but also serves to promote positive influences that are specifically tailored to the particular medical conditions that are associated with the specific user. It can be seen that through the mechanisms of the illustrative embodiments, customized or tailored filtering/blocking/replacement of content is performed based on each user's own individual combination of medical conditions. Thus, the filtering/blocking/replacement may be different for each user depending on their own specific medical conditions.

Figure 2:
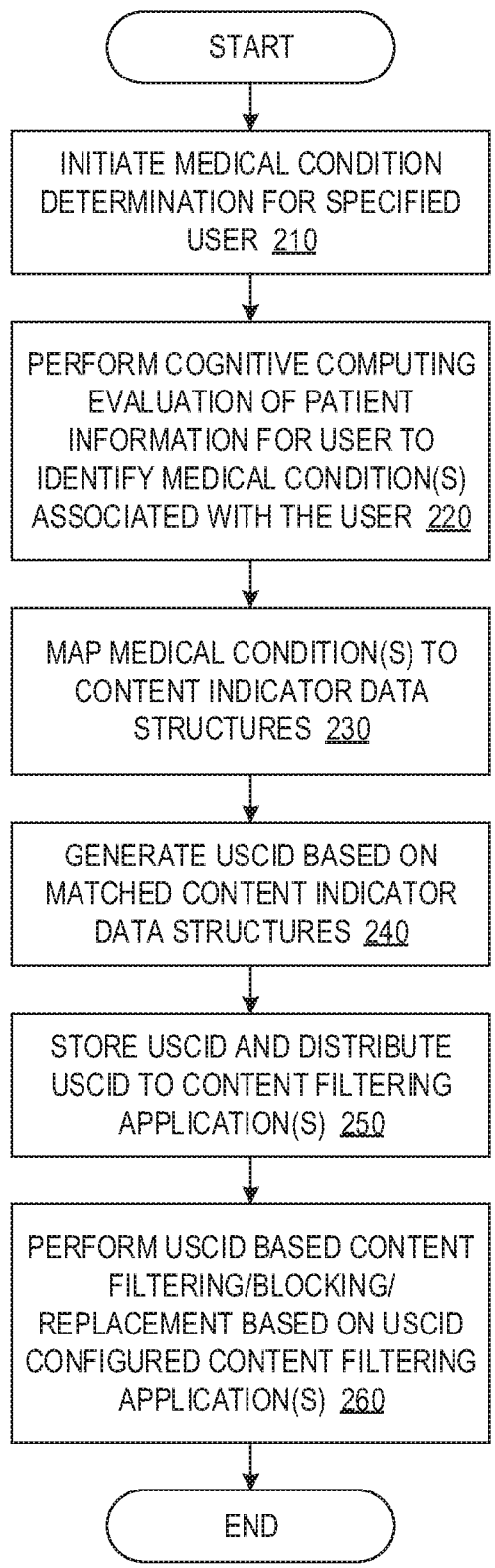
FIG. 2 is a flowchart outlining an example operation of a medical condition content control system in accordance with one illustrative embodiment.

FIG. 2 is a flowchart outlining an example operation of a medical condition content control system in accordance with one illustrative embodiment. As shown in FIG. 2, the operation starts with the initiation of a medical condition determination for a specified user (step 210). For example, this initiation may be in response to a user registering with the medical condition content control system, an expiration of a predetermined time period from a previous update of the medical conditions of a user, or in response to a particular triggering event, e.g., updating of an electronic medical record (EMR) or the like. In response to the initiating of the medical condition determination, the cognitive computing system performs an evaluation of patient information associated with the specified user to identify the medical condition(s) associated with the user (step 220).

Based on the identified medical condition(s) associated with the user as determined by the cognitive computing system, the medical condition(s) are mapped to corresponding content indicator data structures (step 230). The mapped content indicator data structures are used to generate a user specific content indicator dictionary (USCID) data structure for the user (step 240). The USCID is stored in association with the user account and distributed to one or more content filtering applications executing on one or more computing devices used to provide/output content to the user (step 250). The USCID is used to configure the content filtering application(s) and are a basis for filtering/blocking/replacement of content that matches content indicators present in the USCID (step 260). The operation then terminates.

As is apparent from the above description, the present invention is an improved computer tool that specifically improves the way in which electronic content is provided to users via their computing devices by providing an automated content filtering/blocking/replacement mechanism based on a user's medical conditions. The illustrative embodiments may be utilized in many different types of data processing environments. In order to provide a context for the description of the specific elements and functionality of the illustrative embodiments, FIGS. 3-6 are provided hereafter as example environments in which aspects of the illustrative embodiments may be implemented. It should be appreciated that FIGS. 3-6 are only examples and are not intended to assert or imply any limitation with regard to the environments in which aspects or embodiments of the present invention may be implemented. Many modifications to the depicted environments may be made without departing from the spirit and scope of the present invention.

Figure 3:
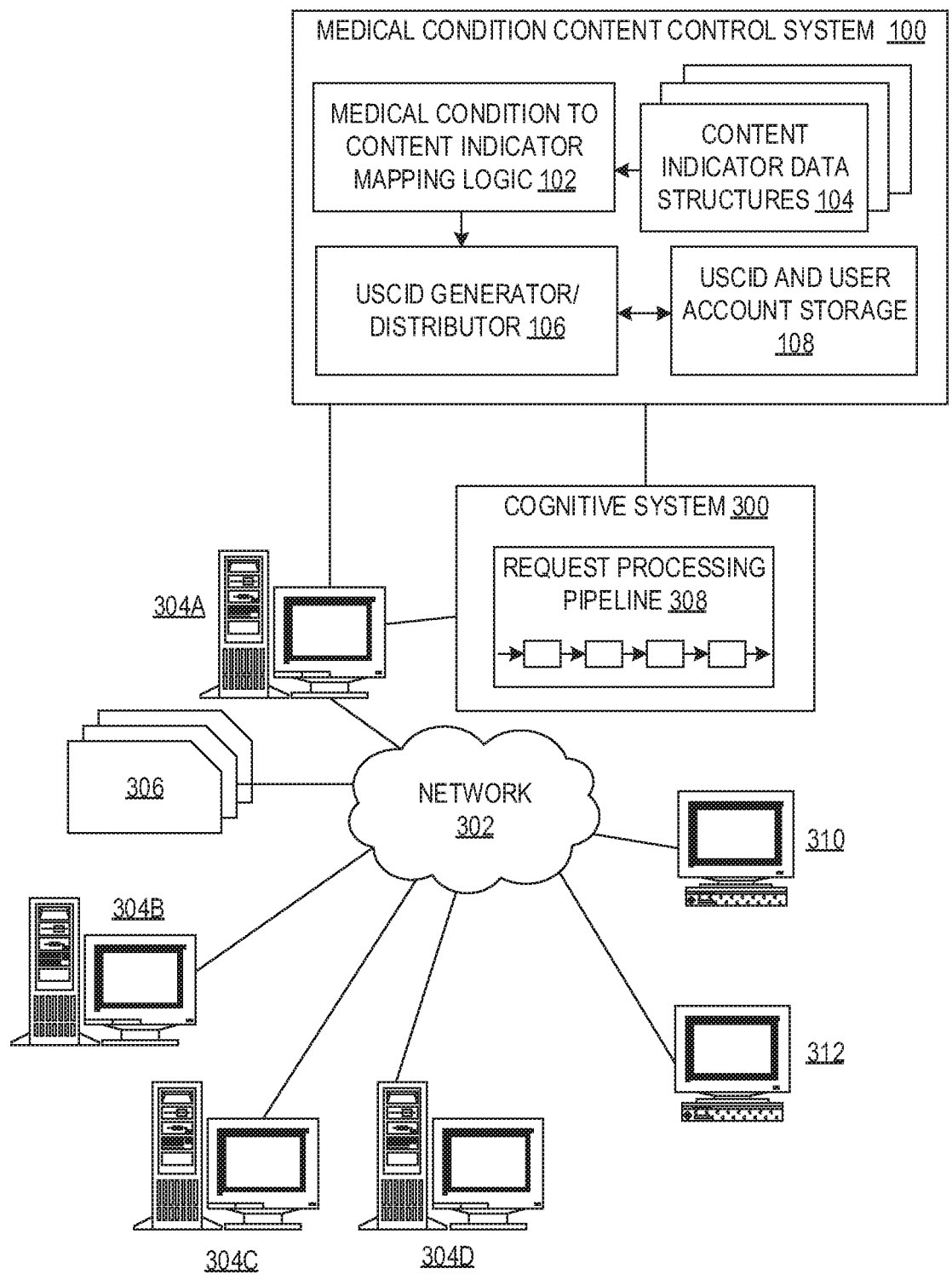
FIG. 3 is a schematic diagram of a distributed data processing system in which a medical condition content control system and cognitive computing system for determining medical conditions associated with users may be implemented in accordance with one illustrative embodiment.

FIG. 3 is a schematic diagram of a distributed data processing system in which a medical condition content control system and cognitive computing system for determining medical conditions associated with users may be implemented in accordance with one illustrative embodiment. As shown in FIG. 3, the cognitive system 300 implements a request processing pipeline 308. The request processing pipeline 308 operates on structured and/or unstructured requests, such as a medical condition request from the medical condition content control system 100. One example of a request processing operation which may be used in conjunction with the principles described herein is described in U.S. Patent Application Publication No. 2011/0125734, which is herein incorporated by reference in its entirety. The cognitive system 300 is implemented on one or more computing devices 304A-D (comprising one or more processors and one or more memories, and potentially any other computing device elements generally known in the art including buses, storage devices, communication interfaces, and the like) connected to the computer network 302. For purposes of illustration only, FIG. 3 depicts the cognitive system 300 being implemented on computing device 304A only, but as noted above the cognitive system 300 may be distributed across multiple computing devices, such as a plurality of computing devices 304A-D. The network 302 includes multiple computing devices 304A-D, which may operate as server computing devices, and 310-312 which may operate as client computing devices, in communication with each other and with other devices or components via one or more wired and/or wireless data communication links, where each communication link comprises one or more of wires, routers, switches, transmitters, receivers, or the like. In some illustrative embodiments, the cognitive system 300 and network 302 enables request processing functionality for one or more cognitive system users, such as medical condition content control system 100. The cognitive system 300 and network 302 may provide other types of cognitive operations including, but not limited to, request processing and cognitive response generation which may take many different forms depending upon the desired implementation, e.g., cognitive information retrieval, training/instruction of users, cognitive evaluation of data, or the like. Other embodiments of the cognitive system 300 may be used with components, systems, sub-systems, and/or devices other than those that are depicted herein.

The cognitive system 300 is configured to implement a request processing pipeline 308 that receives inputs from various sources. The requests may be posed in the form of a natural language question, natural language request for information, natural language request for the performance of a cognitive operation, structured requests, or the like. For example, the cognitive system 300 receives input from the network 302, a corpus or corpora of electronic documents 306, cognitive system users, and/or other data and other possible sources of input. In one embodiment, some or all of the inputs to the cognitive system 300 are routed through the network 302. The various computing devices 304A-D on the network 302 include access points for content creators and cognitive system users. Some of the computing devices 304A-D include devices for a database storing the corpus or corpora of data 306 (which is shown as a separate entity in FIG. 3 for illustrative purposes only). Portions of the corpus or corpora of data 306 may also be provided on one or more other network attached storage devices, in one or more databases, or other computing devices not explicitly shown in FIG. 3. The network 302 includes local network connections and remote connections in various embodiments, such that the cognitive system 300 may operate in environments of any size, including local and global, e.g., the Internet.

In one embodiment, the content creator creates content in a document of the corpus or corpora of data 306 for use as part of a corpus of data with the cognitive system 300. The document includes any file, text, article, or source of data for use in the cognitive system 300. Cognitive system users access the cognitive system 300 via a network connection or an Internet connection to the network 302, and input requests to the cognitive system 300 that are processed based on the content in the corpus or corpora of data 306. The cognitive system 300 parses and interprets the request via a pipeline 308, and provides a response to the cognitive system user, e.g., medical condition content control system 100, containing one or more responses to the request, results of processing the request, or the like. For example, in accordance with one or more illustrative embodiments, the response from the cognitive system 300 comprises one or more medical conditions that are determined to be associated with a user specified in the input request. In some embodiments, the cognitive system 300 provides a response to users in a ranked list of candidate responses while in other illustrative embodiments, the cognitive system 300 provides a single final response or a listing of final responses, e.g., a listing of medical conditions associated with the user specified in the request.

The cognitive system 300 implements the pipeline 308 which comprises a plurality of stages for processing an input request based on information obtained from the corpus or corpora of data 306. The pipeline 308 generates responses for the input request based on the processing of the input request and the corpus or corpora of data 306. The pipeline 308 will be described in greater detail hereafter with regard to FIG. 6.

In some illustrative embodiments, the cognitive system 300 may be the IBM Watson™ cognitive system available from International Business Machines Corporation of Armonk, N.Y., which is augmented with the mechanisms of the illustrative embodiments described hereafter. As outlined previously, a pipeline of the IBM Watson™ cognitive system receives an input request which it then parses to extract the major features of the request, which in turn are then used to formulate queries that are applied to the corpus or corpora of data 306. In one illustrative embodiment, the corpus or corpora of data 306 comprises the patient information from patient information sources 112 in FIG. 1A as well as corpora 114. This information is used by the predictive models employed by the various stages of the pipeline 308 to evaluate extracted features that are indicative of medical conditions associated with the user. Based on the application of the queries to the corpus or corpora of data 306, a set of hypotheses, or candidate responses, e.g., candidate medical conditions associated with the user, to the input request, are generated by looking across the corpus or corpora of data 306 for portions of the corpus or corpora of data 306 (hereafter referred to simply as the corpus 306) that have some potential for containing a valuable response to the input request. The pipeline 308 of the IBM Watson™ cognitive system then performs deep analysis on the language of the input request and the language used in each of the portions of the corpus 306 found during the application of the queries using a variety of reasoning algorithms and predictive models.

The scores obtained from the various reasoning algorithms and predictive models are then weighted against a statistical model that summarizes a level of confidence that the pipeline 308 of the IBM Watson™ cognitive system 300, in this example, has regarding the evidence that the potential candidate answer is inferred by the question. This process is repeated for each of the candidate responses to generate ranked listing of candidate responses which may then be presented to the source of the input request, e.g., medical condition content control system 100, or from which a final answer is selected and presented to the medical condition content control system 100. More information about the pipeline 308 of the IBM Watson™ cognitive system 300 may be obtained, for example, from the IBM Corporation website, IBM Redbooks, and the like. For example, information about the pipeline of the IBM Watson™ cognitive system can be found in Yuan et al., "Watson and Healthcare," IBM developerWorks, 2011 and "The Era of Cognitive Systems: An Inside Look at IBM Watson and How it Works" by Rob High, IBM Redbooks, 2012.

As shown in FIG. 3, the cognitive system 300 operates in conjunction with the medical condition content control system 100, which itself may be implemented as computer logic implemented in specialized hardware, software executed on hardware, or any combination of specialized hardware and software executed on hardware. The medical condition content control system 100 may submit input requests for medical condition information to the cognitive system 300 which may then evaluate the patient information for a user specified in the input request to identify candidate responses representing medical conditions that are likely associated with the user. The candidate responses may be compiled into a listing of medical conditions associated with the user, where the medical conditions are those candidate responses having confidence scores or probability values that are equal to or above predetermined threshold confidence scores or probability values. The resulting medical conditions are returned to the medical condition content control system 100 which then performs its operations as previously described above to generate a USCID and deploy the USCID for content filtering/blocking/replacement by the deployed content filtering application(s).

Figure 4:
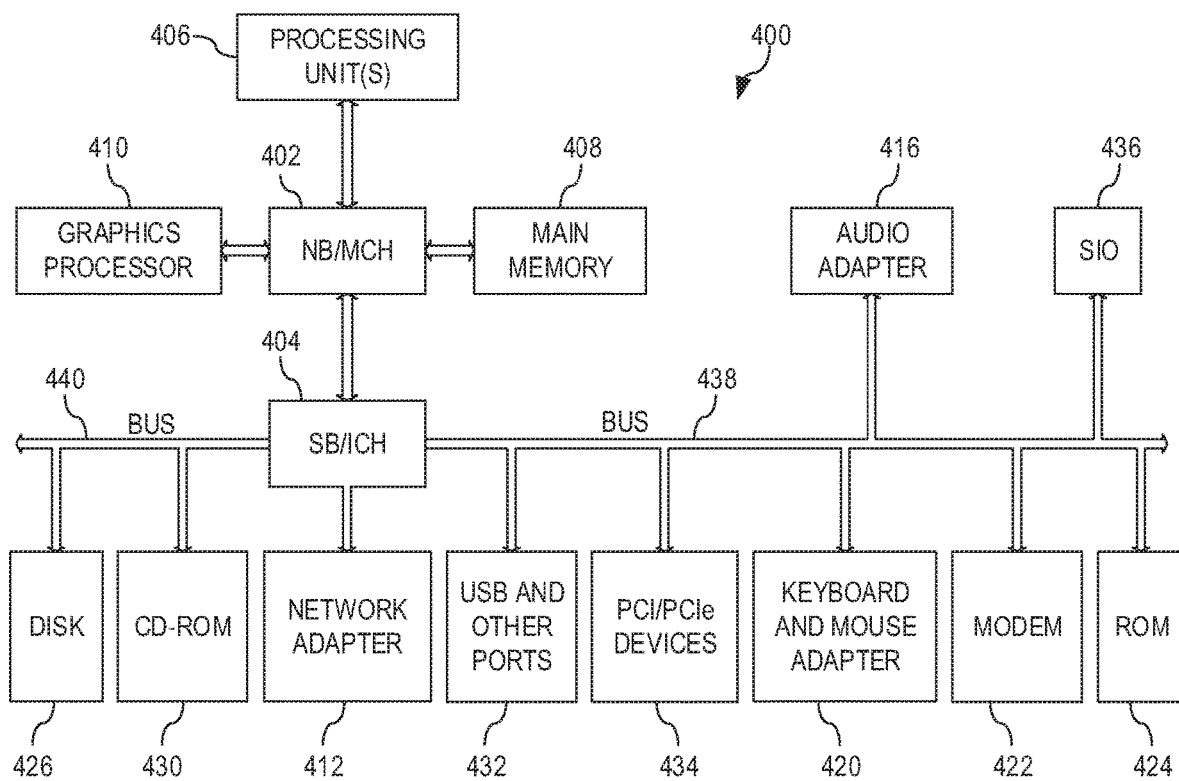
FIG. 4 is a block diagram of an example data processing system in which aspects of the illustrative embodiments are implemented.

As noted above, the mechanisms of the illustrative embodiments are rooted in the computer technology arts and are implemented using logic present in such computing or data processing systems. These computing or data processing systems are specifically configured, either through hardware, software, or a combination of hardware and software, to implement the various operations described above. As such, FIG. 4 is provided as an example of one type of data processing system in which aspects of the present invention may be implemented. Many other types of data processing systems may be likewise configured to specifically implement the mechanisms of the illustrative embodiments.

FIG. 4 is a block diagram of an example data processing system in which aspects of the illustrative embodiments are implemented. Data processing system 400 is an example of a computer, such as server 304A or client 310 in FIG. 3, in which computer usable code or instructions implementing the processes for illustrative embodiments of the present invention are located. In one illustrative embodiment, FIG. 4 represents a server computing device, such as a server 304A, which implements a cognitive system 300 and QA system pipeline 308 augmented to include the additional mechanisms of the illustrative embodiments described hereafter.

In the depicted example, data processing system 400 employs a hub architecture including north bridge and memory controller hub (NB/MCH) 402 and south bridge and input/output (I/O) controller hub (SB/ICH) 404. Processing unit 406, main memory 408, and graphics processor 410 are connected to NB/MCH 402. Graphics processor 410 is connected to NB/MCH 402 through an accelerated graphics port (AGP).

In the depicted example, local area network (LAN) adapter 412 connects to SB/ICH 404. Audio adapter 416, keyboard and mouse adapter 420, modem 422, read only memory (ROM) 424, hard disk drive (HDD) 426, CD-ROM drive 430, universal serial bus (USB) ports and other communication ports 432, and PCI/PCIe devices 434 connect to SB/ICH 404 through bus 438 and bus 440. PCI/PCIe devices may include, for example, Ethernet adapters, add-in cards, and PC cards for notebook computers. PCI uses a card bus controller, while PCIe does not. ROM 424 may be, for example, a flash basic input/output system (BIOS).

HDD 426 and CD-ROM drive 430 connect to SB/ICH 404 through bus 440. HDD 426 and CD-ROM drive 430 may use, for example, an integrated drive electronics (IDE) or serial advanced technology attachment (SATA) interface. Super I/O (SIO) device 436 is connected to SB/ICH 404.

An operating system runs on processing unit 406. The operating system coordinates and provides control of various components within the data processing system 400 in FIG. 4. As a client, the operating system is a commercially available operating system such as Microsoft® Windows 10°. An object-oriented programming system, such as the Java™ programming system, may run in conjunction with the operating system and provides calls to the operating system from Java™ programs or applications executing on data processing system 400.

As a server, data processing system 400 may be, for example, an IBM® eServer™ System p° computer system, running the Advanced Interactive Executive) (AIX®) operating system or the LINUX® operating system. Data processing system 400 may be a symmetric multiprocessor (SMP) system including a plurality of processors in processing unit 406. Alternatively, a single processor system may be employed.

Instructions for the operating system, the object-oriented programming system, and applications or programs are located on storage devices, such as HDD 426, and are loaded into main memory 408 for execution by processing unit 406. The processes for illustrative embodiments of the present invention are performed by processing unit 406 using computer usable program code, which is located in a memory such as, for example, main memory 408, ROM 424, or in one or more peripheral devices 426 and 430, for example.

A bus system, such as bus 438 or bus 440 as shown in FIG. 4, is comprised of one or more buses. Of course, the bus system may be implemented using any type of communication fabric or architecture that provides for a transfer of data between different components or devices attached to the fabric or architecture. A communication unit, such as modem 422 or network adapter 412 of FIG. 4, includes one or more devices used to transmit and receive data. A memory may be, for example, main memory 408, ROM 424, or a cache such as found in NB/MCH 402 in FIG. 4.

Those of ordinary skill in the art will appreciate that the hardware depicted in FIGS. 3 and 4 may vary depending on the implementation. Other internal hardware or peripheral devices, such as flash memory, equivalent non-volatile memory, or optical disk drives and the like, may be used in addition to or in place of the hardware depicted in FIGS. 3 and 4. Also, the processes of the illustrative embodiments may be applied to a multiprocessor data processing system, other than the SMP system mentioned previously, without departing from the spirit and scope of the present invention.

Moreover, the data processing system 400 may take the form of any of a number of different data processing systems including client computing devices, server computing devices, a tablet computer, laptop computer, telephone or other communication device, a personal digital assistant (PDA), or the like. In some illustrative examples, data processing system 400 may be a portable computing device that is configured with flash memory to provide non-volatile memory for storing operating system files and/or user-generated data, for example. Essentially, data processing system 400 may be any known or later developed data processing system without architectural limitation.

Figure 5:
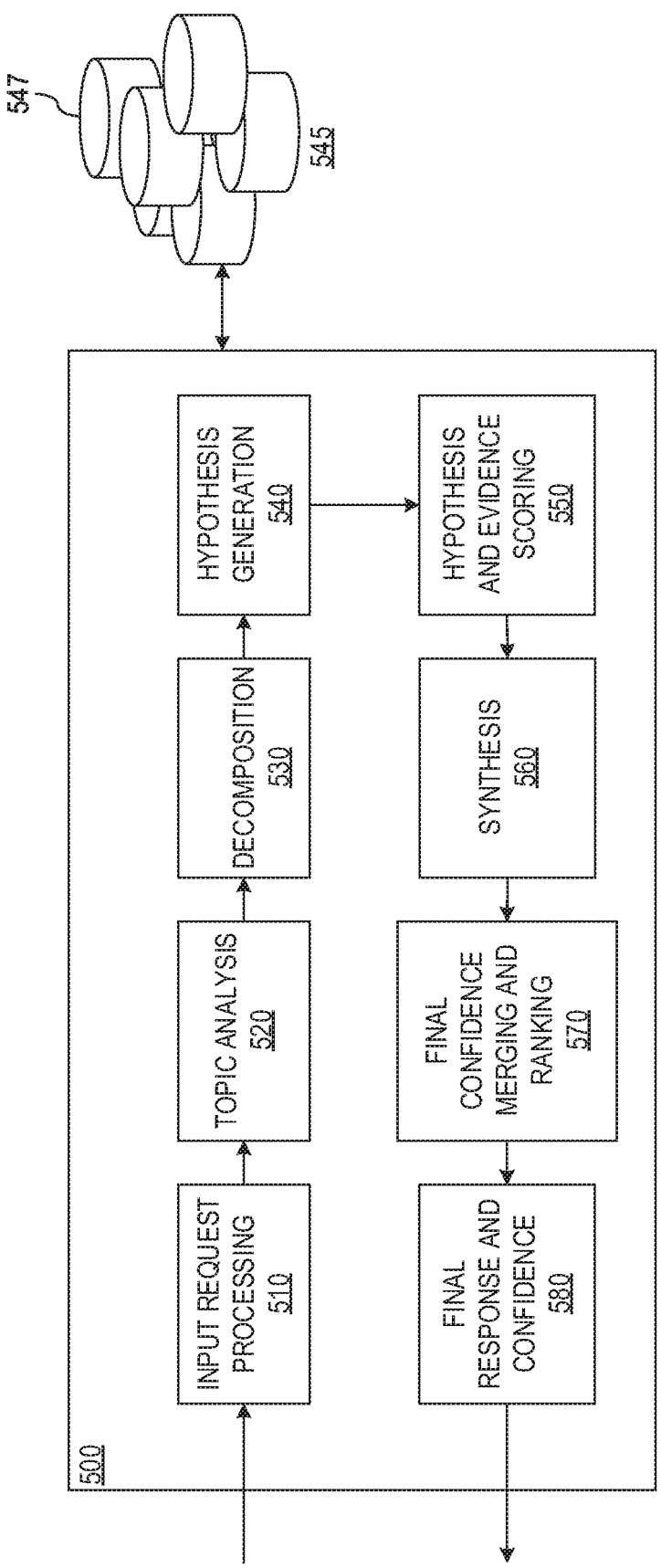
FIG. 5 illustrates an example of a cognitive system processing pipeline used to process an input request in accordance with one illustrative embodiment.

FIG. 5 illustrates an example of a cognitive system processing pipeline used to process an input request in accordance with one illustrative embodiment. The example shown in FIG. 5 is of a question answering pipeline, however the principles and underlying processing performed by such a question answering pipeline may also be applied to other types of requests, such as requests from a medical condition content control system for a listing of medical conditions associated with a specified user. Thus, while the following description may make reference to "questions", these may be any type of structured or unstructured requests that may be parsed to extract features of the request that may be used to determine what is being requested and for whom such that the pipeline may then operate to evaluate patient information to determine medical conditions associated with the specified user. FIG. 5 is provided only as one example of the processing structure that may be implemented to process an input request, which may be provided as a natural language request, a structured request, or a combination of structured and unstructured request, and present a response or result to the input request, such as a listing of medical condition(s) that are associated with a particular user specified in the input request.

The pipeline of FIG. 5 may be implemented, for example, as a pipeline 308 of cognitive system 300 in FIG. 3. It should be appreciated that the stages of the pipeline shown in FIG. 5 are implemented as one or more software engines, components, or the like, which are configured with logic for implementing the functionality attributed to the particular stage. Each stage is implemented using one or more of such software engines, components or the like. The software engines, components, etc. are executed on one or more processors of one or more data processing systems or devices and utilize or operate on data stored in one or more data storage devices, memories, or the like, on one or more of the data processing systems.

As shown in FIG. 5, the pipeline 500 comprises a plurality of stages 510-580 through which the cognitive system operates to analyze an input question and generate a final response. In an initial question input stage 510, the pipeline 500 receives an input request that, for purposes of the depicted example, is presented in a natural language format. That is, an input request may be received from the medical condition content control system 100 for which a listing of medical conditions is to be generated. This input request may be a natural language request or question, e.g., "What medical conditions are associated with John Doe?", as a natural language statement, e.g., "Identify medical conditions associated with John Doe", or as a structured request, e.g., "(John Doe, Medical Conditions)."

In response to receiving the input request, the next stage of the pipeline 500, i.e. the topic analysis stage 520, parses the input request, such as by using natural language processing (NLP) techniques, to extract major features from the input request, and classify the major features according to types, e.g., names, dates, or any of a plethora of other defined topics. For example, in the example question above, the term "John Doe" may be associated with a topic for "persons" and "proper name" indicating that the this is a person for which information is being sought, "medical conditions" may be identified as a type of information being sought.

The identified major features are then used during the decomposition stage 530 to decompose the input request into one or more queries that are applied to the corpora of data/information 545 in order to generate one or more hypotheses or candidate responses, i.e. candidate medical conditions in the illustrative embodiments. The queries are generated in any known or later developed query language, such as the Structure Query Language (SQL), or the like. The queries are applied to one or more databases storing information as electronic texts, files, documents, articles, websites, and the like, that make up the corpora of data/information 545. That is, these various sources themselves, different collections of sources, and the like, represent a different corpus 547 within the corpora 545. There may be different corpora 547 defined for different collections of electronic documents, data files, and the like, based on various criteria depending upon the particular implementation. For example, different corpora may be established for different topics, subject matter categories, sources of information, or the like. As one example, a first corpus may be associated with healthcare documents for type 2 diabetes while a second corpus may be associated with healthcare documents for obesity. In some cases, the corpus may include the electronic medical records and/or other patient information for users.

The queries are applied to one or more databases storing electronic texts, documents, articles, websites, files, and the like, that make up the corpus of data/information, e.g., the corpus of data 306 in FIG. 3. The queries are applied to the corpus of data/information at the hypothesis generation stage 540 to generate results identifying potential hypotheses for answering the input question, which can then be evaluated. That is, the application of the queries results in the extraction of portions of the corpus of data/information matching the criteria of the particular query. These portions of the corpus are then analyzed and used, during the hypothesis generation stage 540, to generate hypotheses for responding to the input request. These hypotheses are also referred to herein as "candidate responses" for the input request. For any input request, at this stage 540, there may be hundreds of hypotheses or candidate responses generated that may need to be evaluated.

The pipeline 500, in stage 550, then performs a deep analysis of each hypothesis or "candidate response" and performs evidence scoring to evaluate the likelihood that the particular hypothesis or candidate response is a correct response for the input request. For example, the candidate response may be a medical condition which is likely to be associated with the specified user while the evidence scoring may be based on a further deep analysis of patient information to determine support for the candidate response being a valid medical condition for the user. As mentioned above, this involves using a plurality of reasoning algorithms and/or predictive models (PMs), each performing a separate type of analysis of the language of the input question and/or content of the corpus that provides evidence in support of, or not in support of, the hypothesis. Each reasoning algorithm/PM generates a score based on the analysis it performs which indicates a measure of relevance of the individual portions of the corpus of data/information extracted by application of the queries as well as a measure of the correctness of the corresponding hypothesis, i.e. a measure of confidence in the hypothesis. There are various ways of generating such scores depending upon the particular analysis being performed.

In the synthesis stage 560, the large number of scores generated by the various reasoning algorithms/PMs are synthesized into confidence scores or confidence measures for the various hypotheses. This process involves applying weights to the various scores, where the weights have been determined through training of the statistical model employed by the pipeline 500 and/or dynamically updated. The weights themselves may be specified by subject matter experts or learned through machine learning processes that evaluate the significance of characteristics evidence passages and their relative importance to overall candidate answer generation. The weighted scores are processed in accordance with a statistical model generated through training of the pipeline 500 that identifies a manner by which these scores may be combined to generate a confidence score or measure for the individual hypotheses or candidate responses. This confidence score or measure summarizes the level of confidence that the pipeline 500 has about the evidence that the candidate response is inferred by the input request, i.e. that the candidate response is the correct response for the input request.

The resulting confidence scores or measures are processed by a final confidence merging and ranking stage 570 which compares the confidence scores and measures to each other, compares them against predetermined thresholds, or performs any other analysis on the confidence scores to determine which hypotheses/candidate responses are the most likely to be the correct response to the input question. The hypotheses/candidate responses are ranked according to these comparisons to generate a ranked listing of hypotheses/candidate responses (hereafter simply referred to as "candidate responses"). From the ranked listing of candidate responses, at stage 580, a final response and confidence score, or final set of responses and confidence scores, are generated and output to the medical condition content control system.

Figure 6:
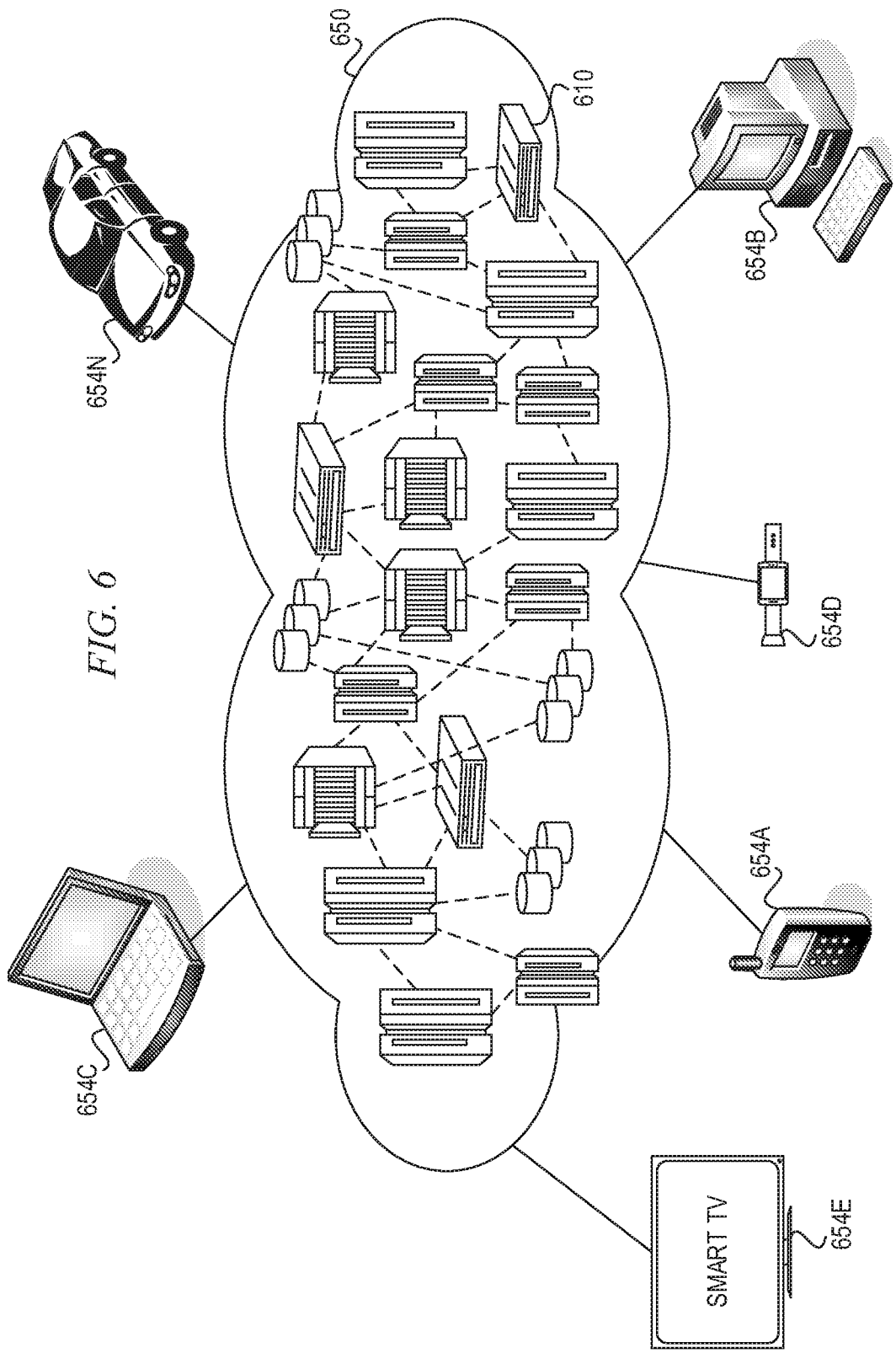
FIG. 6 depicts a cloud computing environment according an illustrative embodiment.

The mechanisms of the illustrative embodiments may also be employed in a cloud computing environment where such content filtering/blocking/replacement is performed as a cloud service to one or more client computing devices, server computing devices, or the like. FIG. 6 depicts a cloud computing environment according an illustrative embodiment. It should be understood in advance that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based email). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 6, illustrative cloud computing environment 650 is depicted. As shown, cloud computing environment 650 comprises one or more cloud computing nodes 610 with which local computing devices used by cloud consumers, such as, for example, personal digital assistant (PDA) or cellular telephone 654A, desktop computer 654B, laptop computer 654C, a smart watch or other Internet enabled wearable device 654D, a smart or Internet enabled television 654E, and/or automobile computer system 654N, may communicate. It should be appreciated that these are only examples of devices with which the cloud computing environment 650 may operate and other devices, such as other Internet of Things (IoT) devices, may be used without departing from the spirit and scope of the present invention. Nodes 610 may communicate with one another. They may be grouped (not shown) physically or virtually, in one or more networks, such as Private, Community, Public, or Hybrid clouds as described hereinabove, or a combination thereof. This allows cloud computing environment 650 to offer infrastructure, platforms and/or software as services for which a cloud consumer does not need to maintain resources on a local computing device. It is understood that the types of computing devices 654A-N shown in FIG. 6 are intended to be illustrative only and that computing nodes 610 and cloud computing environment 650 can communicate with any type of computerized device over any type of network and/or network addressable connection (e.g., using a web browser).

Figure 7:
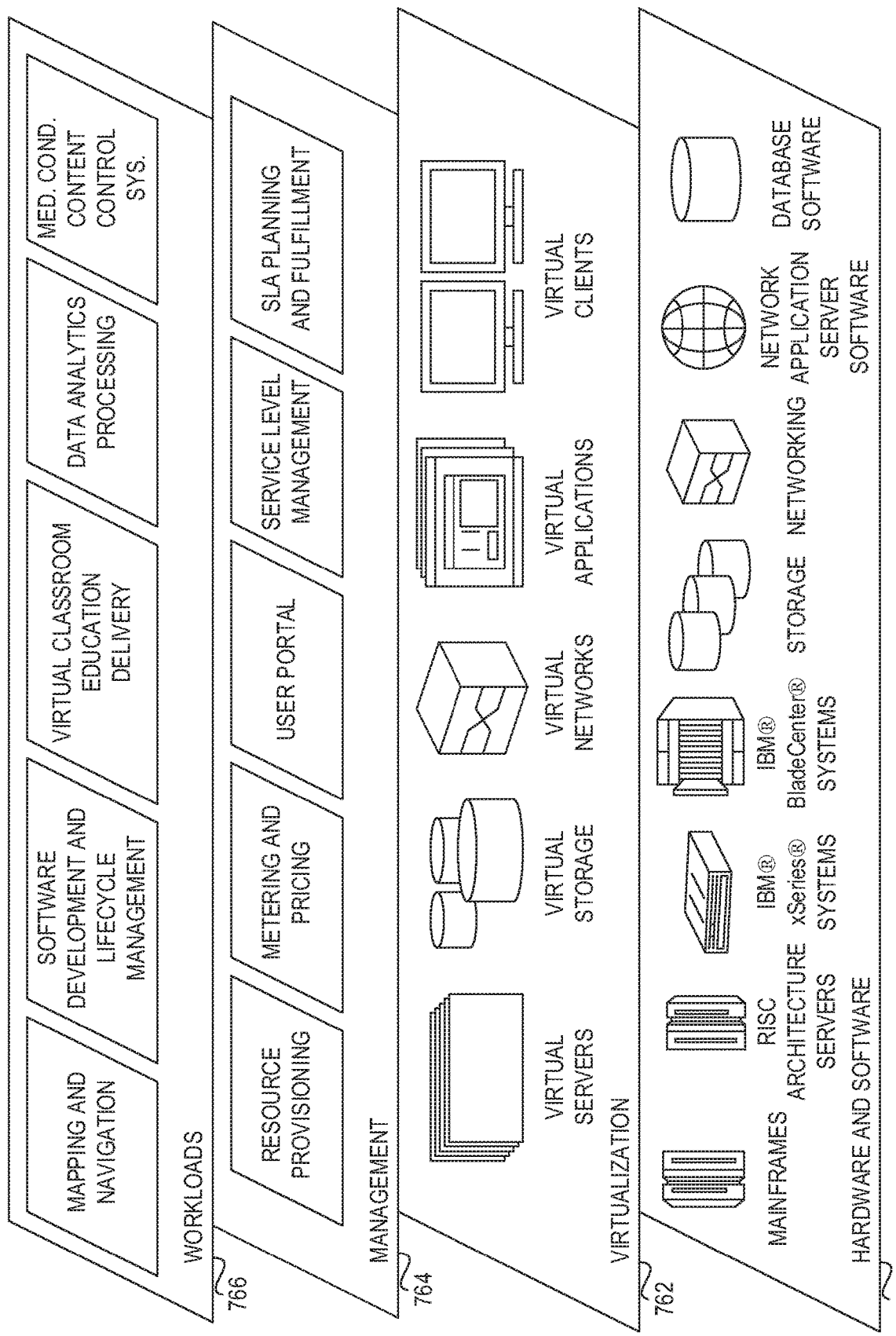
FIG. 7 depicts abstraction model layers according to an illustrative embodiment.

Referring now to FIG. 7, a set of functional abstraction layers provided by cloud computing environment 650 (FIG. 6) is shown. It should be understood in advance that the components, layers, and functions shown in FIG. 7 are intended to be illustrative only and embodiments of the invention are not limited thereto. As depicted, the following layers and corresponding functions are provided:

Hardware and software layer 760 includes hardware and software components. Examples of hardware components include mainframes, in one example IBM® zSeries® systems; RISC (Reduced Instruction Set Computer) architecture based servers, in one example IBM pSeries® systems; IBM xSeries® systems; IBM BladeCenter® systems; storage devices; networks and networking components. Examples of software components include network application server software, in one example IBM WebSphere® application server software; and database software, in one example IBM DB2® database software. (IBM, zSeries, pSeries, xSeries, BladeCenter, WebSphere, and DB2 are trademarks of International Business Machines Corporation registered in many jurisdictions worldwide).

Virtualization layer 762 provides an abstraction layer from which the following examples of virtual entities may be provided: virtual servers; virtual storage; virtual networks, including virtual private networks; virtual applications and operating systems; and virtual clients.

In one example, management layer 764 may provide the functions described below. Resource provisioning provides dynamic procurement of computing resources and other resources that are utilized to perform tasks within the cloud computing environment. Metering and Pricing provide cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal provides access to the cloud computing environment for consumers and system administrators. Service level management provides cloud computing resource allocation and management such that required service levels are met. Service Level Agreement (SLA) planning and fulfillment provide pre-arrangement for, and procurement of, cloud computing resources for which a future requirement is anticipated in accordance with an SLA.

Workloads layer 766 provides examples of functionality for which the cloud computing environment may be utilized. Examples of workloads and functions which may be provided from this layer include: mapping and navigation; software development and lifecycle management; virtual classroom education delivery; data analytics processing; transaction processing; and medical condition content control in accordance with one or more of the illustrative embodiments described above.

As noted above, it should be appreciated that the illustrative embodiments may take the form of an entirely hardware embodiment, an entirely software embodiment or an embodiment containing both hardware and software elements. In one example embodiment, the mechanisms of the illustrative embodiments are implemented in software or program code, which includes but is not limited to firmware, resident software, microcode, etc.

A data processing system suitable for storing and/or executing program code will include at least one processor coupled directly or indirectly to memory elements through a communication bus, such as a system bus, for example. The memory elements can include local memory employed during actual execution of the program code, bulk storage, and cache memories which provide temporary storage of at least some program code in order to reduce the number of times code must be retrieved from bulk storage during execution. The memory may be of various types including, but not limited to, ROM, PROM, EPROM, EEPROM, DRAM, SRAM, Flash memory, solid state memory, and the like.

Input/output or I/O devices (including but not limited to keyboards, displays, pointing devices, etc.) can be coupled to the system either directly or through intervening wired or wireless I/O interfaces and/or controllers, or the like. I/O devices may take many different forms other than conventional keyboards, displays, pointing devices, and the like, such as for example communication devices coupled through wired or wireless connections including, but not limited to, smart phones, tablet computers, touch screen devices, voice recognition devices, and the like. Any known or later developed I/O device is intended to be within the scope of the illustrative embodiments.

Network adapters may also be coupled to the system to enable the data processing system to become coupled to other data processing systems or remote printers or storage devices through intervening private or public networks. Modems, cable modems and Ethernet cards are just a few of the currently available types of network adapters for wired communications. Wireless communication based network adapters may also be utilized including, but not limited to, 802.11 a/b/g/n wireless communication adapters, Bluetooth wireless adapters, and the like. Any known or later developed network adapters are intended to be within the spirit and scope of the present invention.

The description of the present invention has been presented for purposes of illustration and description, and is not intended to be exhaustive or limited to the invention in the form disclosed. Many modifications and variations will be apparent to those of ordinary skill in the art without departing from the scope and spirit of the described embodiments. The embodiment was chosen and described in order to best explain the principles of the invention, the practical application, and to enable others of ordinary skill in the art to understand the invention for various embodiments with various modifications as are suited to the particular use contemplated. The terminology used herein was chosen to best explain the principles of the embodiments, the practical application or technical improvement over technologies found in the marketplace, or to enable others of ordinary skill in the art to understand the embodiments disclosed herein.

What is claimed is:

1. A method, in a data processing system comprising at least one processor and at least one memory, wherein the at least one memory comprises instructions that are executed by the at least one processor to configure the at least one processor to implement a medical condition based content filter engine, the method comprising:

executing a machine learning training operation on at least one predictive computer model of an artificial intelligence (AI) cognitive computing system to train the at least one predictive computer model to predict a probability that a patient has at least one medical condition based on a plurality of different features, extracted from patient information, and input to the at least one predictive computer model, to thereby generate at least one trained predictive computer model;

automatically processing, by the at least one trained predictive computer model of the AI cognitive computing system, an extracted set of features from received patient information associated with a patient to identify one or more medical conditions associated with the patient;

automatically executing mapping logic, on the one or more medical conditions associated with the patient, which maps the one or more medical conditions with one or more medical condition content indicator data structures, wherein the one or more medical condition content indicator data structures comprise at least one negative content indicator identifying content that negatively impacts a health of the patient based on the one or more medical conditions;

automatically generating, by the medical condition based content filter engine, a user specific content indicator dictionary (USCID) data structure by combining the one or more medical condition content indicator data structures mapped to the one or more medical conditions associated with the patient;

automatically configuring a content filtering application executing on a user computing system with the USCID data structure to thereby cause the content filtering application to implement negative content indicators specified in the USCID data structure, wherein the content filtering application executes to filter content to remove portions of the content that matches one or more negative content indicators specified in the USCID data structure;

automatically processing, by the configured content filtering application, received content, received from a content provider computing system via one or more data networks, based on the USCID data structure, to remove portions of the content matching the one or more negative content indicators, thereby generating modified content; and automatically outputting the modified content to a content access application executing on the user computing system.

2. The method of claim 1, wherein the extracted set of features comprise at least one of medical codes, medical terms/phrases, vital sign values, medical lab results, or features of medical images obtained through image analysis.

3. The method of claim 1, further comprising automatically extracting the extracted set of features by at least one of executing computer natural language processing, by natural language processing logic specifically configured to analyze medical data in patient information, on natural language content of the patient information, or performing computerized image analysis on medical image data in the patient information, to extract the extracted set of features from the patient information.

4. The method of claim 1, wherein the at least one trained predictive computer model comprises at least one trained neural network, and wherein automatically processing the extracted set of features comprises:

generating, by the at least one trained neural network of the at least one predictive computer model, a probability score for each medical condition in the at least one medical condition based on a weighted evaluation of the extracted set of features; and comparing the probability score for each medical condition to a threshold probability value to identify the one or more medical conditions associated with the patient as medical conditions for which an associated probability score equals or exceeds the threshold probability value.

5. The method of claim 1, wherein:

the extracted features, in the extracted set of features, further comprise temporal characteristics associated with the extracted features that are extracted from the patient information and evaluated by the automatic processing when identifying the one or more medical conditions, the temporal characteristics are evaluated, by the at least one trained predictive computer model, to identify long term medical conditions that are associated with the patient based on a first classification of temporal characteristics by the at least one trained predictive computer model, and short term medical conditions that are no longer associated with the patient based on a second classification of temporal characteristics by the at least one trained predictive computer model, and the one or more medical conditions associated with the patient are identified based on whether a medical condition corresponding to the patient is a long term medical condition associated with the patient or a short term medical condition that is no longer associated with the patient.

6. The method of claim 1, wherein automatically processing received content based on the USCID data structure further comprises replacing an original portion of the content matching the one or more negative content indicators with replacement content that does not match the one or more negative content indicators, wherein the modified content comprises the replacement content in place of the original portion of the content matching the one or more negative content indicators.

7. The method of claim 6, wherein replacing the original portion of content matching the one or more negative content indicators with replacement content comprises:

mapping a negative content indicator matched by the original portion of content to a corresponding positive content indicator; and retrieving, from a registered content database, the replacement content based on a matching of the positive content indicator with a content indicator associated with the replacement content.

8. A computer program product comprising a computer readable storage medium having a computer readable program stored therein, wherein the computer readable program, when executed on a data processing system, causes the data processing system to:

execute a machine learning training operation on at least one predictive computer model of an artificial intelligence (AI) cognitive computing system to train the at least one predictive computer model to predict a probability that a patient has at least one medical condition based on a plurality of different features, extracted from patient information, and input to the at least one predictive computer model, to thereby generate at least one trained predictive computer model;

automatically process, by at least one trained predictive computer model of the AI cognitive computing system, an extracted set of features from received patient information associated with a patient to identify one or more medical conditions associated with the patient;

automatically execute mapping logic, on the one or more medical conditions associated with the patient, which maps the one or more medical conditions with one or more medical condition content indicator data structures, wherein the one or more medical condition content indicator data structures comprise at least one negative content indicator identifying content that negatively impacts a health of the patient based on the one or more medical conditions;

automatically generate a user specific content indicator dictionary (USCID) data structure by combining the one or more medical condition content indicator data structures mapped to the one or more medical conditions associated with the patient;

automatically configure a content filtering application executing on a user computing system with the USCID data structure to thereby cause the content filtering application to implement negative content indicators specified in the USCID data structure, wherein the content filtering application executes to filter content to remove portions of the content that matches one or more negative content indicators specified in the USCID data structure;

automatically process, by the configured content filtering application, received content, received from a content provider computing system via one or more data networks, based on the USCID data structure, to remove portions of the content matching the one or more negative content indicators, thereby generating modified content; and automatically output the modified content to a content access application executing on the user computing system.

9. The computer program product of claim 8, wherein the extracted set of features comprise at least one of medical codes, medical terms/phrases, vital sign values, medical lab results, or features of medical images obtained through image analysis.

10. The computer program product of claim 8, wherein the computer readable program further causes the data processing system to automatically extract the extracted set of features by at least one of executing computer natural language processing, by natural language processing logic specifically configured to analyze medical data in patient information, on natural language content of the patient information, or performing computerized image analysis on medical image data in the patient information, to extract the extracted set of features from the patient information.

11. The computer program product of claim 8, wherein the at least one trained predictive computer model comprises at least one trained neural network, and wherein automatically processing the extracted set of features comprises:
generating, by the at least one trained neural network of the at least one predictive computer model, a probability score for each medical condition in the at least one medical condition based on a weighted evaluation of the extracted set of features; and
comparing the probability score for each medical condition to a threshold probability value to identify the one or more medical conditions associated with the patient as medical conditions for which an associated probability score equals or exceeds the threshold probability value.

12. The computer program product of claim 8, wherein:
the extracted features, in the extracted set of features, further comprise temporal characteristics associated with the extracted features that are extracted from the patient information and evaluated by the automatic processing when identifying the one or more medical conditions,
the temporal characteristics are evaluated, by the at least one trained predictive computer model, to identify long term medical conditions that are associated with the patient based on a first classification of temporal characteristics by the at least one trained predictive computer model, and short term medical conditions that are no longer associated with the patient based on a second classification of temporal characteristics by the at least one trained predictive computer model, and
the one or more medical conditions associated with the patient are identified based on whether a medical condition corresponding to the patient is a long term medical condition associated with the patient or a short term medical condition that is no longer associated with the patient.

13. The computer program product of claim 8, wherein automatically processing received content based on the USCID data structure further comprises replacing an original portion of the content matching the one or more negative content indicators with replacement content that does not match the one or more negative content indicators, wherein the modified content comprises the replacement content in place of the original portion of the content matching the one or more negative content indicators.

14. The computer program product of claim 13, wherein replacing the original portion of content matching the one or more negative content indicators with replacement content comprises:
mapping a negative content indicator matched by the original portion of content to a corresponding positive content indicator; and
retrieving, from a registered content database, the replacement content based on a matching of the positive content indicator with a content indicator associated with the replacement content.

15. An apparatus comprising:
at least one processor; and
at least one memory coupled to the at least one processor, wherein the at least one memory comprises instructions which, when executed by the at least one processor, cause the at least one processor to implement a medical condition based content filter engine that:
executes a machine learning training operation on at least one predictive computer model of an artificial intelligence (AI) cognitive computing system to train the at least one predictive computer model to predict a probability that a patient has at least one medical condition based on a plurality of different features, extracted from patient information, and input to the at least one predictive computer model, to thereby generate at least one trained predictive computer model;
automatically processes, by at least one trained predictive computer model of the AI cognitive computing system, an extracted set of features from received patient information associated with a patient to identify one or more medical conditions associated with the patient;

automatically executes mapping logic, on the one or more medical conditions associated with the patient, which maps the one or more medical conditions with one or more medical condition content indicator data structures, wherein the one or more medical condition content indicator data structures comprise at least one negative content indicator identifying content that negatively impacts a health of the patient based on the one or more medical conditions;

automatically generates a user specific content indicator dictionary (USCID) data structure by combining the one or more medical condition content indicator data structures mapped to the one or more medical conditions associated with the patient;

automatically configures a content filtering application executing on a user computing system with the USCID data structure to thereby cause the content filtering application to implement negative content indicators specified in the USCID data structure, wherein the content filtering application executes to filter content to remove portions of the content that matches one or more negative content indicators specified in the USCID data structure;

automatically processes, by the configured content filtering application, received content, received from a content provider computing system via one or more data networks, based on the USCID data structure, to remove portions of the content matching the one or more negative content indicators, thereby generating modified content; and automatically outputs the modified content to a content access application executing on the user computing system.

16. The method of claim 1, wherein the at least one negative content indicator comprises at least one of a particular term or phrase, metadata, or data annotations that specify a portion of content to have potential to negatively impact the health of patients having a corresponding medical condition.

17. The method of claim 1, wherein the automatic processing of the received content comprises dynamic automatic processing of a content traffic flow from the content provider computing system to the user computing system.

18. The method of claim 1, wherein the received content is multi-media content, and wherein automatically processing the received content comprises at least one of skipping scenes, during a playback of the multi-media content, that match the one or more negative content indicators.

19. The method of claim 1, wherein the at least one predictive computer model comprises a plurality of predictive computer models, each predictive computer model in the plurality of predictive computer models being trained by the machine learning training operation to predict a probability that a patient has a corresponding medical condition, and wherein the corresponding medical conditions are different for each predictive computer model in the plurality of predictive computer models.

20. The method of claim 1, wherein the one or more medical condition content indicator data structures further comprise at least one positive content indicator identifying content that positively impacts the health of the patient, and wherein automatically processing the received content further comprises automatically replacing the removed portions of the content with replacement content matching the at least one positive content indicator specified in the one or more medical content indicator data structures.

* * * * *